(12) United States Patent
Lee et al.

(10) Patent No.: US 7,138,428 B2
(45) Date of Patent: Nov. 21, 2006

(54) COMPOUNDS ISOLATED FROM GAMBOGE RESIN HAVING ACTIVITY IN INHIBITING THE GROWTH OF TUMOR/CANCER CELLS AND PHARMACEUTICAL COMPOSITIONS COMPRISING THE SAME

(75) Inventors: Sen-Bin Lee, Tauyuan (TW); Chiu-Ming Chen, Hsinchu (TW)

(73) Assignee: Taiwan Sunpan Biotechnology Development Company, Ltd., Tauyuan (TW)

( * ) Notice: Subject to any disclaimer, the term of this patent is extended or adjusted under 35 U.S.C. 154(b) by 0 days.

(21) Appl. No.: 10/958,349

(22) Filed: Oct. 6, 2004

(65) Prior Publication Data

US 2005/0261363 A1   Nov. 24, 2005

(30) Foreign Application Priority Data

May 21, 2004   (TW) ................................ 93114351 A

(51) Int. Cl.
*A61K 31/35*   (2006.01)
(52) U.S. Cl. ...................... 514/453; 514/559; 549/384
(58) Field of Classification Search ................ 549/384; 514/453, 559
See application file for complete search history.

(56) References Cited

U.S. PATENT DOCUMENTS 6,462,041 B1   10/2002   Cai et al.

FOREIGN PATENT DOCUMENTS

EP   0 428 815 A1   5/1991

OTHER PUBLICATIONS

Zhi, Influence of a different processes on bactericidal and tumoricidal effects of gamboges, (1996) PMID:9388932.*
Ito, Xanthones as inhibitors of Epstein-Barr virus activation, Cancer Letters 132 (1998) 113-117.*
"Betulinic Acid," ACS:Betulinic Acid, http://www.cancer.org/docroot/ETO/content/ETO_5_3x_Betulinic_Acid.asp?sitearea=..., Jul. 18, 2003.
"Pharmacology fo Betulinic Acid," Cyberbotanica: Betulinic Acid, http://biotech.icmb.utexas.edu/botany/betul.html, Jul. 18, 2003.
Koichi Yamashita et al., "Effect of three triterpenoids, lupeol, betulin, and betulinic acid on the stimulus-induced superoxide generation and tyrosyl phosphorylation of proteins in human neutrophils," Clinica Chimica Acta 325 (2002), pp. 91-96.
Darrick S. H. L. Kim et al., "Synthesis of Betulinic Acid Derivatives with Activity Against Human Melanoma," Bioorganic & Medicinal Chemistry Letters 8 (1998), pp. 1707-1712.
Simone Fulda et al., "Activation of Mitochondria and Release of Mitochondrial Apoptogenic Factors by Betulinic Acid," The Journal of Biological Chemistry, vol. 273, No. 51, Issue of Dec. 18, 1998, pp. 33942-33948.
G. I. Saitl et al., "Betulinic acid reduces ultraviolet-C-induced DNA breakage in congenital melanocytic naeval cells: evidence for a potential role as a chemopreventive agent," Melanoma Research, vol. 11, 2001, pp. 99-104.
Philippe Bernard et al., "Ethnopharmacology and bioinformatic combination for leads discovery: application to phospholipase $A_2$ inhibitors," Phytochemistry 58 (2001) pp. 865-874.
Valentina Zuco et al., "Selective cytotoxicity of betulinic acid on tumor cell lines, but not on normal cells," Cancer Letters 175 (2002), pp. 17-25.
Arnab Roy Chowdhury et al., "Betulinic acid, a potent inhibitor of eukaryotic topoisomerase I: identification of the inhibitory step, the major functional group responsible and development of more potent derivatives," www.MEDSCIMONIT.com, 2002, pp. BR254-260.

* cited by examiner

*Primary Examiner*—Amelia A. Owens
(74) *Attorney, Agent, or Firm*—Pillsbury Winthrop Shaw Pittman LLP

(57) ABSTRACT

Disclosed herein are an acetone-extracted product obtained from gamboge resin and compounds further purified from said acetone-extracted product, including a new compound called formoxanthone A. The acetone-extracted product and the further purified compounds have been demonstrated to have activities in inhibiting the growth of tumor/cancer cells. Also disclosed are the processes for obtaining said further purified compounds, and the uses of the acetone-extracted product and the further purified compounds in the preparation of pharmaceutical composition for inhibiting the growth of tumor/cancer cells.

16 Claims, 5 Drawing Sheets

COMPOUNDS ISOLATED FROM GAMBOGE RESIN HAVING ACTIVITY IN INHIBITING THE GROWTH OF TUMOR/CANCER CELLS AND PHARMACEUTICAL COMPOSITIONS COMPRISING THE SAME

CROSS-REFERENCE TO RELATED APPLICATION

This application claims priority of Taiwanese Application No. 093114351, filed on May 21, 2004.

BACKGROUND OF THE INVENTION

1. Field of the Invention

The invention relates to an acetone-extracted product obtained from gamboge resin and compounds further purified from the acetone-extracted product, including a new compound called formoxanthone A. The acetone-extracted product and the further purified compounds have been demonstrated to have activities in inhibiting the growth of tumor/cancer cells. The invention also relates to processes for obtaining the further purified compounds, and uses of the acetone-extracted product and the further purified compounds in the preparation of pharmaceutical compositions for inhibiting the growth of tumor/cancer cells.

2. Description of the Related Art

Gamboge resin is the gamboge of *Garcinia* sp. secreted by the plant *Garcinia* of the family Guttiferae. It has been used as a source of vegetative dyes and pigments since the old days. It is also used in folk medicine in some areas such as India and Thailand.

*Garcinia* (TENGHUANG in pinyin), which is commonly known as gamboge, is a kind of evergreen trees that grow in tropical regions. The main species grown in India is *Garcinia morella* Desv, whereas the main species grown in Thailand is *G. harburyi* Hook. Before the flowering-period, the bark of the tree is cut open in a spiral shape about 2 meters from the ground to collect the exuding resin. The resin is then subjected to heat-drying to result in a solidified gamboge resin.

According to traditional Chinese medicine (TCM), gamboge is effective in combating inflammations, clearing away toxins, stopping blood bleeding, and killing worms. Ever since 1934, there have been a number of reports on the components of the gamboge resin. At present, it is known that many compounds can be isolated from extracts of gamboge resin, including: morellin, morellic acid, gambogic acid, morellinol, isomorellin, isomorellic acid, isogambogic acid, isomorellinol, neogambogic acid, desoxymorellin, dihydroisomorellin, α-guttiferin, and β-guttiferin, etc.

Some studies have reported the cytotoxic activity of certain components of gamboge resin on human lung cancer cells (HEL cells), human cervical cancer cells (HeLa cells), and human nasopharyngeal cancer cells (KB cells) [M. Tada et al. (1996), *Phytochemistry*, 41, 815–920; G. A. Cordell et al. (1993), *Magnetic Resonance in Chemistry*, 31, 340–347].

It is pointed out in a report that the roots of *Anemone raddeana* are used in Chinese folk medicine to cure rheumatism and neuralgia, and that betulin and betulinic acid can be isolated from ethanol extracts of the roots of *Anemone raddeana*. Betulin has been proven to be capable of preventing tyrosyl phosphorylation of proteins in human neutrophils, thereby suppressing superoxide generation [K. Yamashita et al. (2002), *Clinica Chimica Acta*, 325, 91–96].

In a report by Darrick S. H. L. Kim et al. in *Bioorganic & Medicinal Chemistry Letters* (1998), 8, 1707–1712, it has been demonstrated that simple modifications of the parent structure of betulinic acid can produce derivatives that can be developed as potent anticancer drugs. There are reports which point out that betulinic acid can trigger apoptosis by a direct effect on mitochondria [Simone Fulda et al. (1998), *The Journal Of Biological Chemistry*, 278, 33942–33948], and has selective cytotoxicity on tumor cells [Valentina Zuco et al. (2002), *Cancer Letters*, 175, 17–25].

To the applicants' knowledge, there has not been any report or patent that discloses the isolation of betulin and betulinic acid from gamboge resin.

U.S. Pat. No. 6,462,041 has disclosed gambogic acid, its analogs and derivatives as represented by the following Formulae I, II and III:

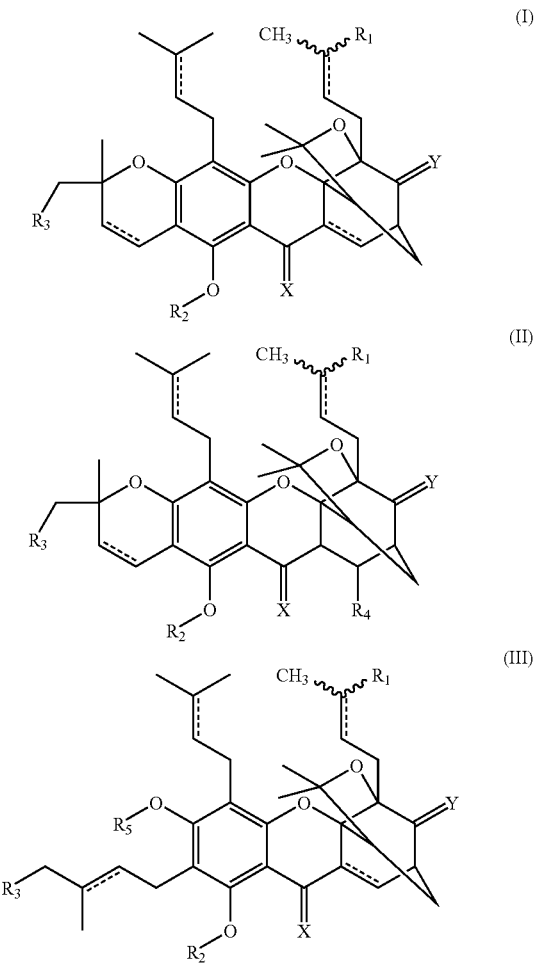

wherein $R_1$ to $R_5$ are such as defined in the aforesaid patent.

Compounds having one of the aforesaid Formula I–III are disclosed to be activators of caspases and inducers of apoptosis.

EP 0 428 815 A1 discloses a process of purifying a cytolytic toxin from the resin of *Garcinia morella* Desv, which relates to a product identified by the name GMD1630 that is obtained by ethanol extraction, chloroform extraction, and thin layer chromatography (TLC). However, the patent does not disclose whether the GMD1630 product is a single compound or a mixture of compounds with similar properties.

In view of the foregoing, the preparation of bioactive extracts or purified compounds from gamboge resin for the manufacture of drugs, such as anticancer drugs, should merit further study and research.

SUMMARY OF THE INVENTION

This invention provides an acetone-extracted product from gamboge resin, and nine compounds further purified from the acetone-extracted product: betulin, betulinic acid, morellic acid, isomorellic acid, gambogic acid, isogambogic acid, isomorellinol, desoxymorellin, and a new compound that is identified as formoxanthone A.

The acetone-extracted product from gamboge resin according to this invention and the compounds further purified there from have been demonstrated to be capable of effectively inhibiting the growth of tumor/cancer cells. Therefore, this invention further provides a pharmaceutical composition comprising a therapeutically effective amount of any of the following:
  (i) an acetone-extracted product from gamboge resin;
  (ii) formoxanthone A; and
  (iii) formoxanthone A and and at least a compound selected from the following compounds: betulin, betulinic acid, morellic acid, isomorellic acid, gambogic acid, isogambogic acid, isomorellinol, and desoxymorellin.

BRIEF DESCRIPTION OF THE DRAWINGS

Other features and advantages of the present invention will become apparent in the following detailed description of the preferred embodiment with reference to the accompanying drawings, in which.

DETAILED DESCRIPTION OF THE PREFERRED EMBODIMENTS

Figure 1:
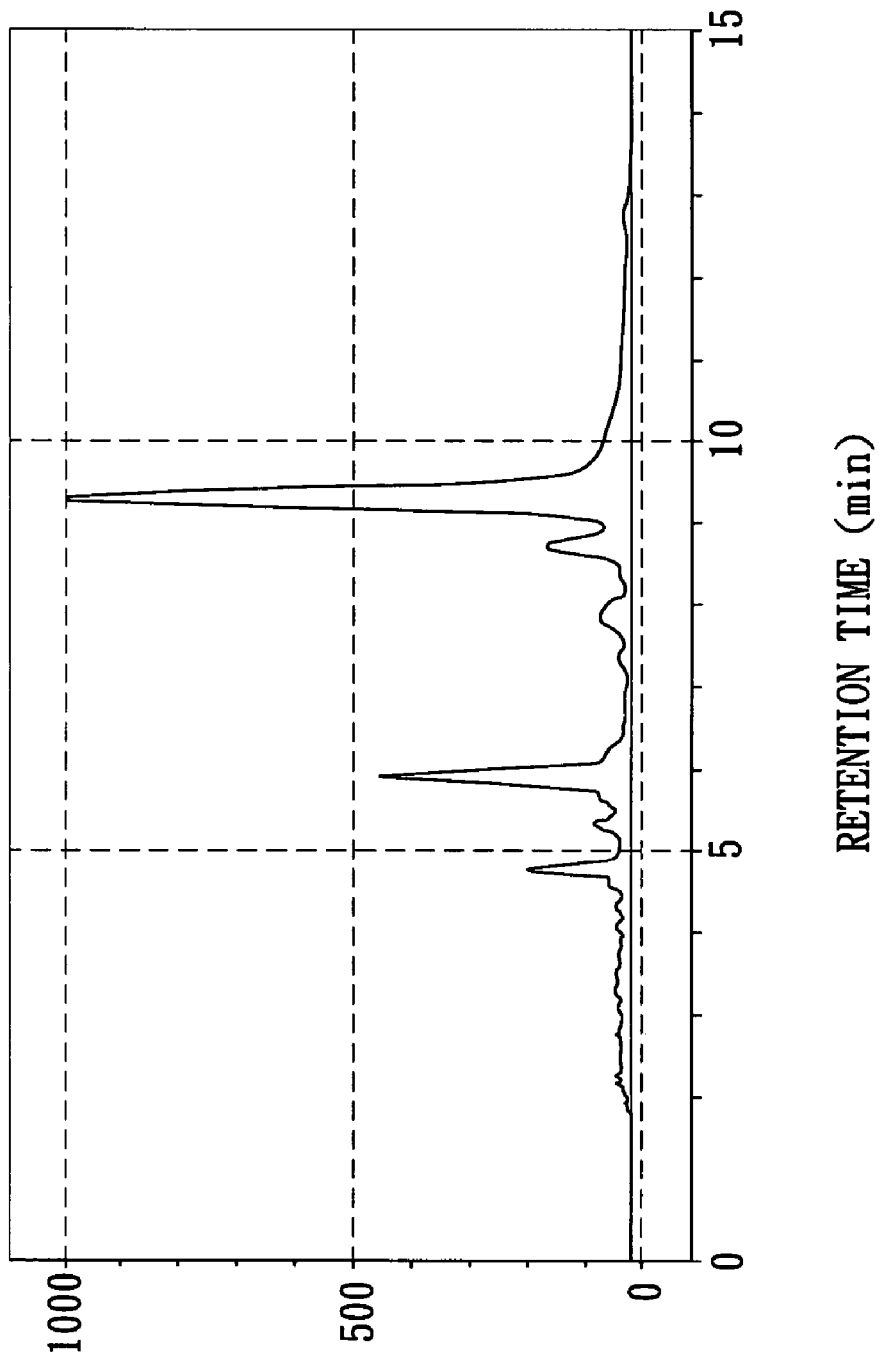
FIG. 1 is an HPLC elution profile of an acetone-extracted product from gamboge acid according to this invention, which is identified as TSB-14 in the following description.

In consideration of the solubility of gamboge resin powder in extraction solvent and the boiling point and safety of the extraction solvent, acetone seemed to be a best choice. The applicants hence tried to extract gamboge resin using acetone and then removing the acetone so as to obtain an acetone-extracted product, which was identified as TSB-14.

Further component separation of the acetone-extracted product TSB-14 was conducted mainly by column chromatography. Preferred choices of suitable column packing agents include commonly used silica gel and Sephadex LH-20. The former is an adsorption matrix, whereas the latter is a column packing agent for size exclusion chromatography.

The acetone-extracted product TSB-14 was first subjected to adsorption chromatography using a silica gel column, and was eluted at n-hexane/ethyl acetate gradient, 100/0→4/1. That is, elution was first performed with n-hexane. Then, the ethyl acetate gradient was gradually increased to obtain three fractions, namely, GME1, GME2 and GME3, in which, as described hereinbelow in connection with Example 2, GME1 was the eluted portion 100/0→10/1; GME2 was the eluted portion 10/1→4/1; and GME3 was the eluted portion 4/1→1/1.

The elution solvent used in the aforesaid fractions of GME1, GME2, and GME3 was removed using a vacuum rotary evaporator.

During the process of fractionation, detection of each fraction was performed using thin layer chromatography (TLC) and developing reagents, and the component separation of each fraction was detected with reference to general operating procedures.

Fraction GME2 was subjected to molecular sieve chromatography using a column filled with Sephadex LH-20. After elution using n-hexane/ethyl acetate/methanol (2:1:1), according to TLC detection, molecular sieve chromatography (n-hexane/ethyl acetate/methanol at 2:1:1) and silica gel column chromatography (gradient elution with n-hexane/ethyl acetate/methanol, 1:1:0→0:1:0→0:10:1) were repeated for the 23rd tube. During elution by silica gel column chromatography, two colorless needle-like crystal products were obtained, which were identified as TSB-0 and TSB-1. In addition, the 46th tube was subjected to thin layer chromatograph. Separated portions corresponding to pink spots that were detected by spray reagents (see Example 2 and Table A hereinbelow) on the TLC sheet were collected, and molecular sieve chromatography and silica gel column chromatography were repeated. Lastly, preparative thin layer chromatography was conducted to obtain two products, which were respectively identified as TSB-6 and TSB-7. Further, the 47th tube was subjected to thin layer chromatography. Separated portions corresponding to pink spots that were detected by spray reagents (see Example 2 and Table A hereinbelow) on the TLC sheet were collected, and molecular sieve chromatography and silica gel column chromatography were repeated. Lastly, molecular sieve chromatography and recrystallization were conducted to obtain an orange flake-like crystal, which was identified as TSB-2. In addition, the 63rd tube was subjected to silica gel column chromatography, and was eluted with dichloromethane/methanol (30:1) for subsequent preparative thin layer chromatography (n-hexane/ethyl acetate, 2:1) and recrystallization to obtain a yellow needle-like product, which was identified as TSB-4.

The fraction GME1 was subjected to silica gel column chromatography, and was eluted with n-hexane/acetone (5:1). The 26th tube was subjected to molecular column chromatography (n-hexane/ethyl acetate/methanol, 2:1:1) and then preparative thin layer chromatography to obtain two products, which were identified as TSB-5 and TSB-3, respectively. In addition, the 23rd tube and the 51st tube were respectively subjected to silica gel column chromatography. The former was eluted with n-hexane/dichloromethane (1:1). The latter was eluted with n-hexane and n-hexane/ethyl acetate (7:1) gradient. Thereafter, TCL was performed. Separated portions corresponding to pink spots shown on the TLC sheet and having equivalent Rf values were combined to undergo silica gel column chromatography and elution with dichloromethane. Then, TLC was performed, and the separated portions which were shown as pink spots on the TLC sheet were collected for subsequent chromatographies (including silica gel and molecular column chromatographies) Finally, preparative thin layer chromatography and recrystallization were performed to obtain an orange needle-like product, which was identified as TSB-8.

The nine purified products thus obtained hereinabove were subjected to spectrum analysis, including infrared spectroscopy, nuclear magnetic resonance spectroscopy ($^1$H- and $^{13}$C-NMR), mass spectrometry, etc.

Products TSB-0 and TSB-1 have been confirmed by chemical structure analyses to be two known betulinic acid derivatives, namely betulin and betulinic acid, which respectively have the following chemical structures:

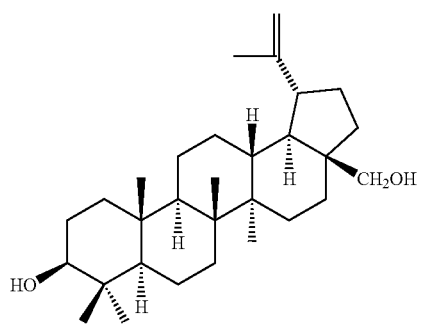

TSB-0 (betulin)

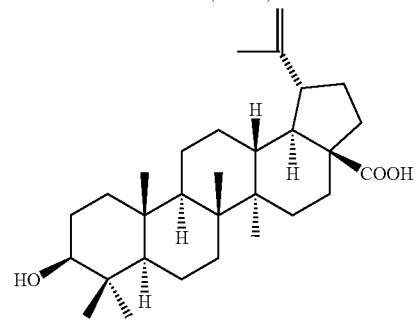

TSB-1 (betulinic acid)

Products TSB-7 and TSB-2 have been confirmed by chemical structure analysis to be two known morellic acid stereoisomers, i.e., morellic acid and isomorellic acid, which respectively have the following chemical structures:

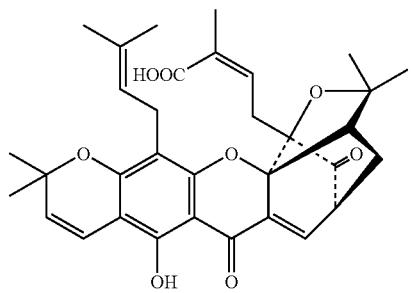

TSB-7 (morellic acid)

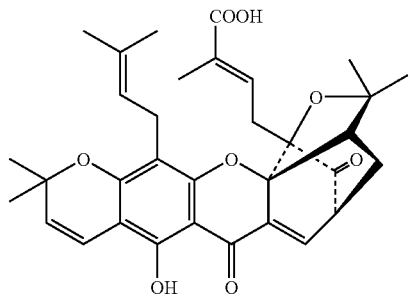

TSB-2 (isomorellic acid)

Products TSB-5 and TSB-3 have been confirmed by chemical structure analysis to be two known morellic acid stereoisomers, i.e., gambogic acid and isogambogic acid, which respectively have the following chemical structures:

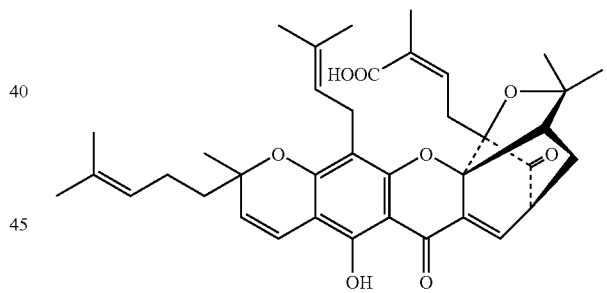

TSB-5 (gambogic acid)

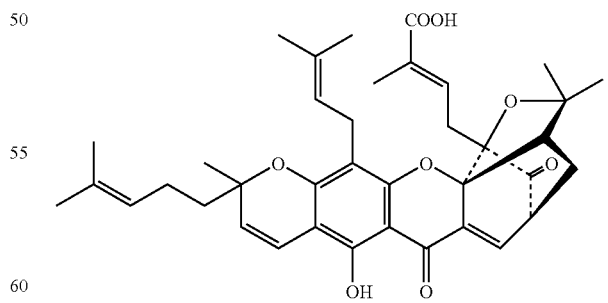

TSB-3 (isogambogic acid)

Product TSB-6 has been confirmed by chemical structure analysis to be isomorellinol, which has the following chemical structure:

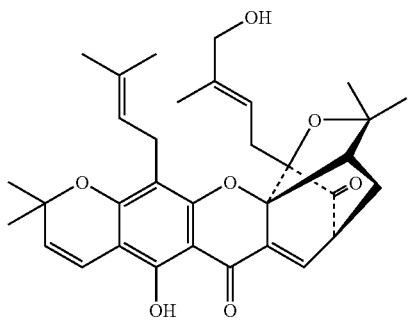

TSB-6 (isomorellinol)

Product TSB-8 has been confirmed by chemical structure analysis to be desoxymorellin, which has the following chemical structure:

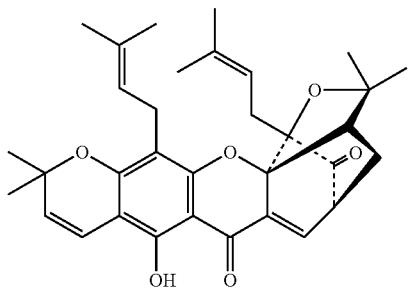

TSB-8 (desoxymorellin)

It has been confirmed by the result of chemical structure analysis and a comparison with the spectroscopic data of known compounds that TSB-4 is a novel compound that is hitherto not reported. It is herein named as formoxanthone A, and has the following chemical structure:

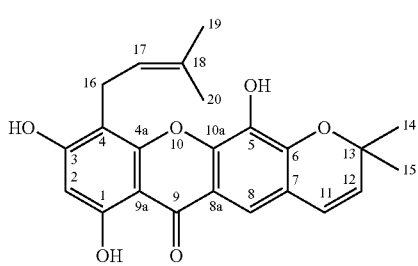

The product TSB-4 (formoxanthone A) obtained from gamboge resin according to the invention has, in the xanthone skeleton: (1) three hydroxyl groups respectively at C-1 position, C-3 position and C-5 position; (2) one γ,γ-dimethylallyl chain at C-4 position; (3) one 2,2-dimethylpyran ring located at C-6 position and C-7 position; and (4) one di-substituted double bond between C-11 position and C-12 position and one tri-substituted double bond between C-17 position and C-18 position.

According to the aforesaid chemical structure, formoxanthone A derivatives having the following general formula can be prepared by chemical reactions:

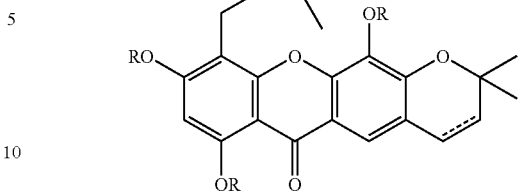

wherein R independently represents hydrogen; an optionally substituted lower alkyl, preferably having 1–6 carbon atoms; an optionally substituted aryl having 3–20 carbon atoms, preferably $C_5$–$C_{12}$ aryl; an optionally substituted aralkyl having 3–30 carbon atoms, preferably ($C_5$–$C_{12}$) aryl ($C_1$–$C_6$) alkyl, more preferably ($C_6$)aryl ($C_1$–$C_3$) alkyl; or acyl represented by a chemical formula Ra—CO, wherein Ra is: an optionally substituted lower alkyl, preferably having 1–6 carbon atoms; an optionally substituted aryl having 3–20 carbon atoms, preferably $C_5$–$C_{12}$ aryl; an optionally substituted aralkyl having 3–30 carbon atoms, preferably ($C_5$–$C_{12}$)aryl($C_1$–$C_6$)alkyl, and more preferably ($C_6$) aryl ($C_1$–$C_3$) alkyl.

For example, since the aforesaid hydroxyl groups are located on an aromatic ring, methoxy drviatives can be obtained by methylation, or acetyl derivatives can be obtained by acetylation. In addition, as for the double bonds located outside the xanthone ring, the double bonds can be processed via hydrogenation to generate hydrogenated derivatives, or hydroxyl derivatives can be generated by other addition reactions, such as hydration. On the other hand, peroxidation can be used to generate epoxide derivatives, such as one having the following chemical structure:

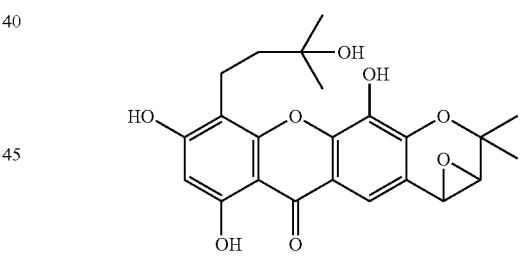

The applicants further investigated the bioactivities of the acetone-extracted product obtained from gamboge resin according to the invention, nine products (TSB-0 to TSB-8) obtained by further purifying the acetone-extracted product, and a mixture composed of the purified products, and discovered that the acetone-extracted product, the products TSB-2 to TSB-8, and the mixture composed of the aforesaid products are effective in inhibiting the growth of tumor/cancer cells (such as liver cancer cells, lung cancer cells, breast cancer cells, colon cancer cells, leukemia cells, lymphoma cancer cells, etc.) In the inhibition of growth of tumor/cancer cells, although products TSB-0 and TSB-1 may not be as effective as products TSB-2 to TSB-8, the applicants discovered that when they are used in combination with other products, products TSB-0 and TSB-1 seemed to have an effect of activating other products. Therefore, products TSB-0 and TSB-1 are contemplated to be used as an activator in a pharmaceutical composition comprising at least one of products TSB-2 to TSB-8.

According to publications, betulin and betulinic acid of triterpenes have multiple pharmacological activities, including effectiveness against melanoma cancer cells in vitro and in vivo. Furthermore, they are quite safe. Therefore, when used in combination with products TSB-2 to TSB-8 which are xanthone compounds, the two products, TSB-0 and TSB-1, which are triterpene compounds, should be capable of exerting an auxiliary or synergistic effect.

Accordingly, this invention provides a pharmaceutical composition, which comprises a therapeutically effective amount of any of the following:
  (i) an acetone-extracted product from gamboge resin;
  (ii) formoxanthone A; and
  (iii) formoxanthone A and at least a compound selected from the group consisting of betulin, betulinic acid, morellic acid, isomorellic acid, gambogic acid, isogambogic acid, isomorellinol, and desoxymorellin.

In a preferred embodiment, this invention provides a pharmaceutical composition, which includes an acetone extracted product from gamboge resin.

In another preferred embodiment, this invention provides a pharmaceutical composition, which includes formoxanthone A and at least a compound selected from the group consisting of betulin, betulinic acid, morellic acid, isomorellic acid, gambogic acid, isogambogic acid, isomorellinol, and desoxymorellin.

In a more preferred embodiment, this invention provides a pharmaceutical composition, which includes formoxanthone A, morellic acid, isomorellic acid, gambogic acid, isogambogic acid, isomorellinol, desoxymorellin, betulin, and betulinic acid. In another more preferred embodiment, this invention provides a pharmaceutical composition, which includes, based on the weight of the composition, 5% of formoxanthone A, 8% of morellic acid, 8% of isomorellic acid, 18% of gambogic acid, 15% of isogambogic acid, 2% of isomorellinol, 4% of desoxymorellin, 8% of betulin, and 8% of betulinic acid as active components.

The nine products separated and purified from gambogic acid according to this invention include morellinol, desoxymorellin, two betulinic acid derivatives, i.e., betulin and betulinic acid, and two pairs of stereoisomers, i.e., morellic acid and isomorellic acid, and gambogic acid and isogambogic acid. Furthermore, according to the experimental results of extraction and separation, the two stereoisomers of gambogic acid and isogambogic acid have the highest contents, followed by the two stereoisomers of morellic acid and isomorellic acid.

The applicants made various combinations of these nine products according to the structural properties of the compounds, and proved that all of the combinations of the nine products exhibited excellent effects in suppressing growth of cancer cells. Therefore, by making reference to the pharmacological experiment results and by taking into consideration the industrial applicability of the aforesaid nine products, the aforesaid nine products can be formulated into pharmaceutical compositions having different active components and compositional proportions according to the intended effects.

Accordingly, in a preferred embodiment, this invention provides a pharmaceutical composition, which includes formoxanthone A, betulinic acid, and any one of the following combinations of compounds:
  (1) isogambogic acid, gambogic acid, and desoxymorellin;
  (2) isomorellic acid, morellic acid, and isomorellinol;
  (3) gambogic acid, morellic acid, and desoxymorellin; and
  (4) isogambogic acid, isomorellic acid, and isomorellinol.

In a preferred embodiment, this invention provides a pharmaceutical composition, which includes, based on the weight of the composition, 5% formoxanthone A, 10% betulinic acid, 20% isogambogic acid, 50% gambogic acid, and 5% desoxymorellin as active components.

In another preferred embodiment, this invention provides a pharmaceutical composition, which includes, based on the weight of the composition, 5% formoxanthone A, 10% betulinic acid, 20% isomorellic acid, 50% morellic acid, and 5% isomorellinol as active components.

In still another preferred embodiment, this invention provides a pharmaceutical composition, which includes, based on the weight of the composition, 5% formoxanthone A, 10% betulinic acid, 40% gambogic acid, 30% morellic acid, and 5% desoxymorellin as active components.

In yet another preferred embodiment, this invention provides a pharmaceutical composition, which includes, based on the weight of the composition, 5% formoxanthone A, 10% betulinic acid, 40% isogambogic acid, 30% isomorellic acid, and 5% isomorellinol as active components.

The pharmaceutical composition according to this invention can be formulated into a suitable dosage form for parenteral, topical, or oral administration using technology well known to those skilled in the art, which includes, but is not limited to, injections (e.g., sterile aqueous solutions or dispersions), sterile powder, tablets, lozenges, pills, capsules, and the like. In addition, the biologically active components according to this invention can be incorporated into controlled-release drugs and prescriptions.

Optionally, the pharmaceutical composition of this invention can additionally comprise a pharmaceutically acceptable carrier widely employed in the art of drug-manufacturing. For instance, the pharmaceutically acceptable carrier may include one or more of the following agents: solvents (e.g., water, normal saline, buffer solution, glycerin, organic solvents), emulsifiers, suspending agents, disintegrators, binders, excipients, stablizers, preservatives, lubricants, absorption delaying agents, liposomes, and the like.

To produce an oral solid preparation, an excipient and, if necessary, a binder, a disintegrator, a lubricant, a coloring agent, a flavoring agent and/or the like may be admixed with an extract product from the gamboge resin according to this invention. The resultant mixture can then be formed into tablets, coated tablets, granules, powder, capsules or the like by a method known per se in the art. Such additives can be those generally employed in the present field of art, including excipients: saccharide compounds [such as glucose, lactose, sucrose, brown sugar, sorbitol, mannitol, starch], sodium chloride, calcium carbonate, kaolin, micro-crystalline cellulose, and silicic acid; binders: water, ethanol, propanol, sucrose solution, glucose solution, starch solution, gelatin solution, carboxymethylcellulose, hydroxypropylcellulose, hydroxypropylstarch, methylcellulose, ethylcellulose, shellac, calcium phosphate, and polyvinylpyrrolidone; disintegrators: dry starch, sodium alginate, powdered agar, sodium hydrogencarbonate, calcium carbonate, sodium lauryl sulfate, monoglycerol stearate, and lactose; lubricants: purified talc, stearate salts, borax, and polyethylene glycol; and corrigents: sucrose, bitter orange peel, citric acid, and tartaric acid.

In a preferred embodiment according to this invention, the pharmaceutical composition includes a pharmaceutically acceptable excipient. The excipient includes at least a saccharide compound selected from the following groups: sucrose, brown sugar, lactose, sorbitol, mannitol, corn starch, and crystalline cellulose. When saccharide compounds are used as excipients, they can enhance the properties of powder-form pharmaceutical compounds, and have the effect of facilitating dissolution.

To produce an oral liquid preparation, a flavoring agent, a buffer, a stabilizer, and the like may be admixed with an extract product from the gamboge resin according to this invention. The resultant mixture can then be formed into a solution for internal use, a syrup, an elixir or the like by a method known per se in the art. In this case, the flavoring agent can be the same as that mentioned above. Illustrative of the buffer is sodium citrate, while illustrative of the stabilizer are tragacanth, gum arabic, and gelatin.

To prepare an injection, a pH regulator, a buffer, a stabilizer, an isotonicity, and the like may be admixed with an extract product from the gamboge resin according to this invention. The resultant mixture can then be formed into a subcutaneous, intramuscular or intravenous injection by a method known per se in the art. Examples of the pH regulator and the buffer include sodium citrate, sodium acetate, and sodium phosphate. Illustrative of the stabilizer are sodium pyrosulfite, EDTA, thioglycollic acid, and thiolactic acid. Examples of the isotonicity include sodium chloride and glucose.

The term "effective amount" as used herein refers to an amount of the pharmaceutical composition according to this invention which is sufficient to provide a desired therapeutic effect when administered to a treated subject requiring the composition without causing undesirable severe damage to non-targeted tissues or organs. The therapeutically effective amount will change depending on different factors. These factors include, for instance, the type of disease, the weight, age, physical condition and response of the subject to be treated, and the route of administration. The therapeutically effective amount can be readily determined by a person skilled in the art.

The dosage and the frequency of administration of the pharmaceutical composition according to this invention will vary depending on the following factors: the severity of the disease to be treated, the route of administration, and the weight, age, physical condition and response of the subject to be treated. For instance, the daily dosage of the pharmaceutical composition according to this invention may be 2.1 to 3.0 mg per kilogram of the body weight, and may be administered in a single dose or in several doses. When administered in three divided doses, for instance, each dosage is 0.7 to 1.0 mg per kilogram of body weight.

The pharmaceutical composition according to the present invention can be administered singly, or in combination with other therapeutic methods or therapeutic medicaments for use in the treatment of tumors or cancers. Such therapeutic methods include chemotherapy and external beam radiation therapy. Such therapeutic medicaments include, but are not limited to, paclitaxel, cisplatin, carboplatin, cyclophosphamide, and doxorubicin.

The present invention will be described in more detail with reference to the following examples, which are given for the purpose of illustration only and are not intended to limit the scope of the present invention.

EXAMPLES

General Procedures:

Infrared spectra were recorded on a JASCO FT-IR 5300 spectrometer as KBr discs.

Ultraviolet spectra were measured on a HITACHI U-3000 spectrometer.

EIMS spectra were recorded on a JEOL HX110 or a JEOL SX-102A mass spectrometer.

Proton and carbon-13 nuclear magnetic resonance spectra were obtained on a BRUKER AM400, a VARIAN GEMINI-400 or a BRUKER ADVANCE DMX-600 spectrometer.

Column chromatography includes molecular sieve column chromatography using Sephadex LH-20 (Pharmacia Fine Chemicals), and silica gel column chromatography using Merck Kiesegel 60 (70–230 mesh ASTM).

For TLC sheets, Merck Silica gel $60F_{254}$ glass sheets (20×20 cm) having a layer thickness of 0.25 mm and being cuttable into suitable sizes were used.

For preparative layer chromatography (PLC) sheets, Merck Silica gel $60F_{254}$ glass sheets (20×20 cm) having a layer thickness of 0.5 mm or 1 mm were used.

For TLC detection, the following spray reagent formulations were used: (a) $Ce(SO_4)_2 \cdot 4H_2O$ (0.8 g); (b) $(NH_4)_6Mo_7O_{24} \cdot 4H_2O$ (20.0 g); (c) concentrated sulfuric acid (23 mL); and (d) distilled water (377 mL).

Development response was detected using UV lamps for irradiation and at short wavelengths (254 nm) and long wavelengths (365 nm).

High performance liquid chromatography (HPLC) was carried out using Rainin, model SD-200. The detection of UV detector was performed using a fixed wavelength of 360 nm. LiChrospher 100RP-18e 5 μm (Merck) was used as analyzing column. Mobile phase: 90% acetonitrile, and 10% deionized water spiked with 0.05% TFA (v/v); flow rate was 1.0 ml/min; analytical conditions: dissolving sample with acetone to form a suitable diluted solution to be put into the HPLC equipment.

Example 1

Preparation of Acetone-Extracted Product from Gamboge Resin

Extraction Procedures:

Gamboge resin purchased from a local Chinese drugstore was pulverized into powder, and 100 g of the powder was soaked in acetone at room temperature to carry out extraction (6×500 mL), each lasting for 24 hours. The combined extraction solution was filtered using filter paper in normal ambient condition. Acetone was removed from the filtered solution using a vacuum rotary evaporator to obtain a brownish yellow gel-like solid (65 g) (S. A. Ahmad et al. (1966), *Journal Chemical Society (C)*, 772–779).

The acetone-extracted product thus obtained was identified as TSB-14. To understand the distribution of the major components of the product TSB-14, HPLC analysis was conducted on the product TSB-14 according to the aforesaid general procedures, and an HPLC elution profile as shown in FIG. 1 was obtained.

Example 2

Preparation of Purified Compounds from Gamboge Resin

Experimental Procedures:

The column analysis described hereinabove was conducted according to the foregoing general procedures.

35 g of the product TSB-14 obtained in Example 1 was subjected to silica gel column chromatography [column: 10 cm (diameter)×80 cm (length)] and eluted with (n-hexane/ethyl acetate gradient) (100/0→4/1), the solvent being removed using a vacuum rotary evaporator and separated into three fractions, GME1 (10 g) GME2 (14 g), and GME3 (8 g).

GME1 is a fraction collected when n-hexane/ethyl acetate gradient elution was eluted to 100/0→100/10, and was found by detection using TLC (developing solvent: dichloromethane/methanol, 20:1) to contain TSB-5 (vide infra) as a major component and other components having an Rf value in which the Rf value>TSB-5.

GME2 is a fraction collected when n-hexane/ethyl acetate gradient elution was eluted to 10/1→4/1, and was found by detection using TLC (developing solvent: dichloromethane/methanol, 20:1) to contain TSB-5 as a major component, and components TSB-7, TSB-6 and TSB-2 having an Rf value slightly less than that of TSB-5.

GME3 is a fraction collected when n-hexane/ethyl acetate gradient elution was eluted to 4/1→1/1, and was not found to contain TSB-5 when detected using TLC (developing solvent: dichloromethane/methanol, 20:1). It merely contains other components that have larger polarities and an Rf value less than that of TSB-5, and it exhibited a tailing phenomenon.

10 g of the fraction GME2 was used to perform column chromatography using Sephadex LH-20 (column: 5 cm×80 cm), which is hereinafter referred to as column A. After elution using n-hexane/ethyl acetate/methanol (2:1:1) (fraction size: 100 mL), Sephadex LH-20 column chromatography (elution solvent: n-hexane/chloroform/methanol, 2:1:10) was repeated for the 23rd tube of fraction, which was also subjected to a silica gel column chromatography (elution solvent: n-hexane/chloroform/methanol gradient, 1:1:0→0:1:0→0:10:1). Two products, TSB-0 (320 mg) and TSB-1 (450 mg) in the form of colorless needle-like crystals were obtained one after the other during elution using silica gel column chromatography.

In addition, the 46th tube of fraction obtained by eluting column A was used to perform TLC (developing solvent: dichloromethane/methanol, 20:1), and separated portions corresponding to pink spots that were detected on the TLC sheet by spray reagents were collected, and molecular sieve chromatography (n-hexane/ethyl acetate/methanol, 2:2:1) and silica gel column chromatography (elution solvent: n-hexane/ethyl acetate, 4:1) were repeated. Finally, preparative thin layer chromatography (developing solvent: dichloromethane/methanol, 100:1) was performed to obtain product TSB-6 (44 mg) and product TSB-7 (220 mg) which were in the form of orange powders.

In addition, the 47th tube of fraction obtained by eluting column A was used to perform TLC (developing solvent: dichloromethane/methanol, 20:1), and separated portions corresponding to pink spots that were detected on the TLC sheet by spray reagents were collected for performing Sephadex LH-20 column chromatography (elution solvent: n-hexane/ethyl acetate/methanol, 2:2:1). The elution solvent was removed in a vacuum evaporator, and the residue was subjected to silica gel column chromatography (elution solvent: n-hexane/ethyl acetate, 4:1; n-hexane/ethyl acetate 1:0→10:1, gradient elution; n-hexane/ethyl acetate/methanol, 20:30:1). Finally, molecular sieve column chromatography (Sephadex LH-20, elution solvent: n-hexane/ethylacetate/methanol, 2:2:1) was performed. The elution solvent was removed using a vacuum evaporator, and the residue was recrystallized to obtain product TSB-2 (815 mg) in the form of orange yellow flake-like crystals.

In addition, the 63rd tube of the fraction obtained by eluting from column A was used to perform silica gel column chromatography (elution solvent: dichloromethane/methanol, 30:1), followed by TLC, so as to obtain separated portions corresponding to yellow spots that were detected on the TLC sheet (developing solvent: dichloromethane/methanol, 20:1) by spray reagents (heating was performed after spraying the spray reagent; see general operating procedures and Table A). The separated portions were combined, and the elution solvent was removed using a vacuum evaporator. The residue was subjected to preparative thin layer chromatography (developing solvent: n-hexane/ethyl acetate, 2:1) to obtain product TSB-4 (52 mg) in the form of yellowish needle-like crystals.

In addition, the fraction GME1 (8 g) was subjected to silica gel column chromatography (column: 6 cm×80 cm), which is hereinafter referred to as column B. After elution using n-hexane/acetone (5:1) (fraction size: 100 mL). The 26th tube was used to perform molecular sieve column chromatography (elution solvent: n-hexane/ethyl acetate/methanol, 2:2:1), and the elution solvent was removed using a vacuum evaporator. The residue was subjected to preparative thin layer chromatography (developing solvent: n-hexane/ethyl acetate, 4:1) to obtain product TSB-5 (1050 mg) in the form of orange powders, and product TSB-3 (850 mg) in the form of dark yellow powders.

In addition, the 23rd tube and the 51st tube of fraction obtained after eluting from column B were respectively subjected to silica gel column chromatography. The former was eluted with n-hexane/dichloromethane (1:1). The latter was subjected to gradient elution, n-hexane→n-hexane/ethyl acetate (1:0→7:1). TLC was performed to collect separated portions corresponding to pink spots detected on the TLC sheet (developing solvent: n-hexane/acetone, 6:1) by the spray reagent and having identical Rf values. The collected separated portions were combined, and the elution solvent was removed using a vacuum evaporator. The residue was eluted by silica gel column chromatography (elution solvent: dichloromethane). Then, TLC was performed to collect and combine the separated portions that corresponded to pink spots developed on the TLC sheet (developing solvent: n-hexane/acetone, 6:1). The elution solvent was removed using a vacuum evaporator, whereas the residue was subjected to molecular sieve column chromatography (elution solvent: n-hexane/ethyl acetate/methanol, 2:2:1). The elution solvent was removed using a vacuum evaporator. Finally, the residue was subjected to preparative thin layer chromatography (developing solvent: n-hexane/dichloromethane, 2:1) and recrystallization to obtain product TSB-8 (60 mg) in the form of orange needle-like crystals.

Example 3

Identification and Characterization of Compounds Purified from Gamboge Resin

Experimental Procedures:

The physical and chemical properties of the nine products obtained from gamboge resin in Example 2 were analyzed according to the aforesaid general procedures, including infrared spectroscopy (1R), nuclear magnetic resonance spectroscopy ($^1$H- and $^{13}$C-NMR), mass spectrometry (EIMS), and thin layer chromatography (TLC).

Results:

The results of development of the nine products (TSB-0 to TSB-8) obtained in Example 2 on TLC sheets are shown in Table A, in which product TSB-4 is noted to have exhibited a yellow color in all of the tests conducted.

TABLE A

Development results of products obtained from gamboge resin on TLC sheets

| Product number | Color seen with naked eyes after development | Color under UV lamp | Color at room temperature after spraying reagent | Color after spraying reagent and heating |
|---|---|---|---|---|
| TSB-0 | Colorless | colorless | colorless | Blue |
| TSB-1 | Colorless | colorless | colorless | Blue |
| TSB-2 | Yellow, turned pink after standing | Yellow | Yellow | Pink |
| TSB-3 | Yellow | Yellow | Yellow | Green |
| TSB-4 | Yellow | Yellow | Yellow | Yellow |
| TSB-5 | Yellow | Yellow | Yellow | Green |
| TSB-6 | Yellow, turned pink after standing | Yellow | Yellow | Pink |
| TSB-7 | Yellow, turned pink after standing | Yellow | Yellow | Pink |
| TSB-8 | Yellow, turned pink after standing | Yellow | Yellow | Pink |

From the TLC development behavior and the physical and chemical properties as observed, product TSB-4 was preliminarily determined to be a new compound, which has not be described in any documentary publication.

The nine products were subsequently determined by employing various spectroscopic analyses. The experimental data thus obtained are summarized as follows:

1. Product TSB-0:

Product TSB-0 was determined to have the following characteristics (properties):

Colorless needles, mp 257~259° C. IR$v_{max}$ cm$^{-1}$ (KBr): 3400, 3090, 2970, 1640, 1460, 1380, 1040, 1020, 880. $^1$H NMR (CDCl$_3$, 400 MHz): δ4.65 (1H, d, J=2.0 Hz), 4.55 (1H, d, J=2.0 Hz), 3.77 (1H, d, J=10.9 Hz), 3.31 (1H, br d, J=10.9 Hz), 3.16 (1H, dd, J=11.2, 5.0 Hz), 1.66 (3H, s), 1.01, 1.00, 0.95, 0.80, 0.74 (each 3H, s). $^{13}$CNMR (CDCl$_3$, 100 MHz): δ150.62, 109.74, 79.14, 60.80, 55.57, 50.67, 49.05, 47.96, 42.92, 41.16, 38.99, 38.93, 37.56, 37.36, 34.48, 34.10, 30.02, 29.42, 28.09, 27.58, 27.27, 25.48, 21.01, 19.19, 18.44, 16.13, 15.37, 14.87.

EIMSm/z (relative intensity): 442[M]$^+$(76), 427(11), 424 (16), 411(77), 399(12), 385(14), 288(15), 273(6), 271(5), 257(9), 247(10), 245(10), 234(56), 220(30), 207(90), 203 (80), 189(100).

According to the analyzed spectroscopic data, product TSB-0 was identified to be a known compound having the following chemical structure, i.e., betulin:

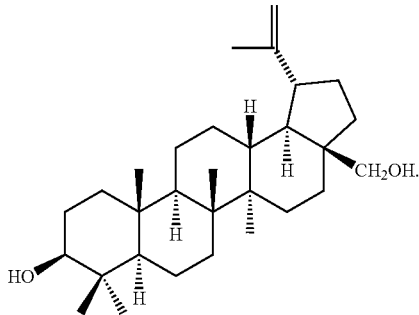

2. Product TSB-1:

Product TSB-1 was determined to have the following properties:

Colorless needles, mp 290~292° C. IR$v_{max}$ cm$^{-1}$ (KBr): 3600–2400, 3070, 2950, 1690, 1640, 1240, 1040, 880. $^1$H NMR (400 MHz, CD$_3$OD): δ0.75, 0.86, 0.95, 0.97, 1.00, 1.70 (each 3H, s), 2.23 (1H, dt, J=12.4, 2.8 Hz), 2.30 (1H, dt, J=12.8, 3.6 Hz), 3.02 (1H, dt, J=10.4, 4.8 Hz), 3.12 (1H, dd, J=11.2, 5.2 Hz), 4.59, 4.71 (each 1H, brs). $^{13}$CNMR (CD$_3$OD-CDCl$_3$, 100 MHz): δ178.93, 150.51, 109.16, 78.53, 55.98, 55.14, 50.31, 46.75, 42.17, 40.41, 38.53, 38.06, 36.88, 34.08, 32.01, 30.32, 29.39, 27.56, 26.66, 25.29, 20.62, 18.94, 18.02, 15.76, 15.56, 15.03, 14.34.

EIMSm/z (relative intensity): 456[M]$^+$(70), 438(35), 423 (25), 410(20), 395(15), 316(15), 302(18), 259(30), 248(80), 234(55), 220(60), 207(80), 203 (60), 189 (100).

According to the analyzed spectroscopic data, product TSB-1 was identified to be a known compound having the following chemical structure, i.e., betulinic acid:

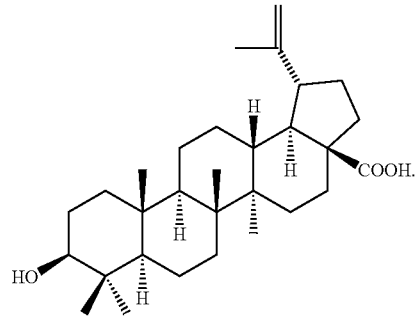

3. Product TSB-2:

Product TSB-2 was detected to have the following properties:

Yellow flakes, mp 204~209° C. IR$v_{max}$ cm$^{-1}$ (KBr): 3500–2400, 2960, 1735, 1680, 1650, 1590, 1430, 1380, 1325, 1130, 1040, 960, 870. $^1$H NMR (CDCl$_3$, 400 MHz): δ7.56 (1H, d, J=6.9 Hz), 6.63 (1H, d, J=9.6 Hz), 5.51 (1H, d, J=9.6 Hz), 5.12 (1H, dd, J=13.6, 6.8 Hz), 3.52 (1H, dd, J=6.2, 4.7 Hz), 3.26 (2H, d, J=7.4 Hz), 2.66 (1H,m), 2.55 (2H,m), 2.35 (1H, dd, J=13.4, 4.6 Hz), 1.75 (3H,s), 1.72 (3H,s), 1.65 (3H,s), 1.44 (3H,s), 1.43 (3H,s), 1.35 (3H,s), 1.30 (3H,s). $^{13}$C NMR (CDCl$_3$, 100 MHz): δ200.93, 178.91, 171.86, 161.10, 157.64, 157.28, 136.97, 135.39, 133.35, 131.70, 128.63, 126.18, 122.12, 115.44, 108.27, 103.18, 100.49, 90.71, 83.71, 83.64, 78.65, 49.06, 46.88, 29.95, 28.93, 28.33, 25.71, 25.31, 21.62, 18.09, 11.34.

EIMS m/z (relative intensity): 560[M]⁺(100), 545(47), 532(22), 517(36), 405(44), 389 (11), 363(24), 349(17), 307(12), 287 (22), 285(16), 245(15), 215(12), 189(5).

According to the analyzed spectroscopic data, product TSB-2 was identified to be a known compound having the following chemical structure, i.e., isomorellic acid:

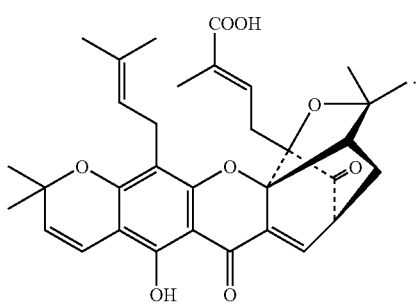

4. Product TSB-3:

Product TSB-3 was determined to have the following properties:

Dark yellow amorphous powder, mp 110~112° C. IRν$_{max}$ cm$^{-1}$ (KBr): 3500–2400, 2960, 2920, 1735, 1685, 1640, 1590, 1435, 1400, 1380, 1330, 1175, 1140, 1045, 960, 805, 760. $^1$H NMR (CDCl$_3$, 400 MHz): δ12.70, 12.69 (1H, s), 7.48 (1H, d, J=6.8 Hz), 6.59 (1H, d, J=10.4 Hz), 6.47 (1H, t, J=7.2 Hz), 5.38, 5.36 (1H, d, J=10.0 Hz), 5.03 (2H, m), 3.44 (1H, m), 3.21 (1H, m), 3.17 (1H, m), 2.56 (1H, m), 2.45 (1H, m), 2.27 (1H, dd, J=12.0, 4.4 Hz), 1.97 (2H, m), 1.67, 1.64, 1.57, 1.54, 1.52, 1.47, 1.32, 1.27 (each 3H, s). $^{13}$C NMR (CDCl$_3$, 100 MHz): δ202.95, 202.88, 178.76, 178.71, 172.38, 172.24, 161.34, 161.21, 157.52, 157.27, 137.07, 136.82, 135.32, 133.23, 133.18, 131.77, 131.70, 131.64, 128.86, 128.49, 124.67, 123.76, 123.69, 122.09, 115.86, 107.82, 102.81, 102.70, 100.38, 100.27, 90.66, 90.55, 83.68, 83.55, 83.51, 81.23, 81.19, 48.95, 46.87, 46.78, 41.83, 29.94, 29.83, 28.97, 28.86, 27.42, 27.27, 25.61, 25.57, 25.37, 25.22, 22.68, 21.55, 18.07, 18.00, 17.53, 11.26.

EIMS m/z (relative intensity): 628[M]⁺(78), 613(11), 600(12), 546(68), 545(100), 517(26), 473(15), 389(8), 355(11), 271(5), 245(12), 214(19), 189(8).

According to the analyzed spectroscopic data, product TSB-3 was identified to be a known compound having the following chemical structure, i.e., isogambogic acid:

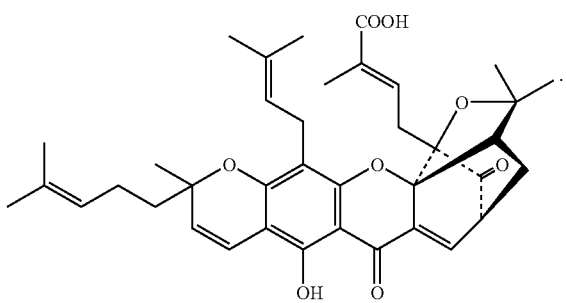

5. Product TSB-5:

Product TSB-5 was detected to have the following properties:

Orange powder; mp 96~99° C. IRν$_{max}$ cm$^{-1}$ (KBr): 3600–2400, 2950, 2910, 1735, 1680, 1625, 1585, 1450, 1430, 1400, 1380, 1325, 1255, 1170, 1135, 1040, 950, 880, 800, 755. $^1$H NMR (CDCl$_3$, 400 MHz): δ12.72, 12.70 (1H, s), 7.51, 7.50 (1H, d, J=6.9 Hz), 6.52, 6.51 (1H, d, J=10.0 Hz), 6.17, 6.07 (1H, t, J=7.4 Hz), 5.34, 5.30 (1H, d, J=10.0 Hz), 5.02 (2H, m), 3.44 (1H, m), 3.26 (1H, m), 3.10 (1H, m), 2.97 (1H, m), 2.88 (1H, m), 2.47 (1H, dd, J=9.2, 2.5 Hz), 1.99 (2H, m), 1.71, 1.70, 1.69, 1.66, 1.54, 1.50, 1.29, 1.22 (each 3H, s). $^{13}$C NMR (CDCl$_3$, 100 MHz): δ203.26, 178.82, 178.78, 171.89, 171.70, 161.35, 161.20, 157.51, 157.45, 157.24, 138.51, 135.52, 135.26, 133.26, 133.11, 131.77, 131.61, 131.29, 131.25, 127.38, 127.34, 124.62, 124.30, 123.79, 122.21, 115.80, 107.64, 107.46, 102.77, 102.60, 100.41, 100.33, 90.97, 90.87, 83.70, 83.58, 81.15, 80.93, 48.92, 46.72, 41.89, 41.59, 29.84, 29.78, 29.15, 28.77, 28.71, 27.55, 26.81, 25.51, 25.55, 25.11, 22.65, 21.52, 20.60, 18.05, 17.97, 17.51.

EIMS m/z (relative intensity): 628[M]⁺(46), 613(7), 600(12), 546(48), 545(100), 517(24), 474(13), 391(7), 355(7), 287(6), 245(9), 214(13), 189(5).

According to the analyzed spectroscopic data, product TSB-5 was identified to be a known compound having the following chemical structure, i.e., gambogic acid:

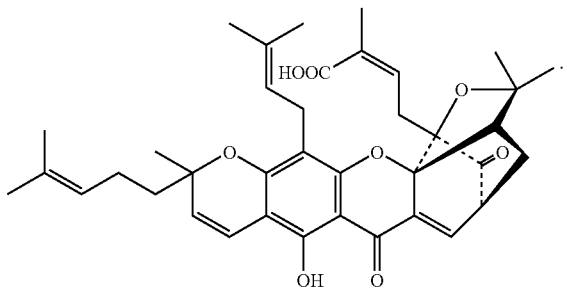

6. Product TSB-6:

Product TSB-6 was determined to have the following properties:

Orange powder; mp 137~139° C. IRν$_{max}$ cm$^{-1}$ (KBr): 3460, 2970, 2925, 1735, 1645, 1630, 1590, 1460, 1435, 1400, 1385, 1330, 1300, 1250, 1210, 1185, 1165, 1140, 1045, 960, 880, 810. $^1$H NMR (CDCl$_3$, 400 MHz): δ12.68 (1H, s), 7.41 (1H, d, J=7.2 Hz), 6.59 (1H, d, J=10.0 Hz), 5.49 (1H, d, J=10.0 Hz), 5.19 (1H, t, J=7.0 Hz), 4.73 (1H, t, J=8.0 Hz), 3.61 (2H, q, J=10.2 Hz), 3.49 (1H, d, J=4.7 Hz), 3.47 (1H, d, J=4.7 Hz), 3.32 (1H, dd, J=14.5, 6.8 Hz), 3.24 (1H, dd, J=14.3, 7.7 Hz), 2.60 (1H, d, J=7.7 Hz), 2.48 (1H, d, J=9.4 Hz), 2.31 (1H, dd, J=13.5, 4.7 Hz), 1.74, 1.68, 1.64, 1.25, 1.01 (each 3H, s), 1.41 (6H, s). $^{13}$C NMR (CDCl$_3$, 100 MHz): δ203.35, 180.33, 161.06, 157.80, 157.44, 138.01, 134.40, 133.63, 131.87, 126.31, 121.90, 118.20, 115.50, 108.44, 103.00, 100.72, 90.48, 84.50, 83.41, 78.66, 67.92, 49.09, 47.00, 30.09, 28.96, 28.28, 28.21, 25.71, 25.29, 21.57, 18.14, 12.49.

EIMS m/z (relative intensity): 546[M]⁺(100), 531(18), 518(44), 503(40), 485(9), 433(7), 405(33), 391(10), 363(19), 349(13), 307(10), 287(25), 245(8), 231(18), 214(12), 189(5), 105(6).

According to the analyzed spectroscopic data, product TSB-6 was identified to be a known compound having the following chemical structure, i.e., isomorellinol:

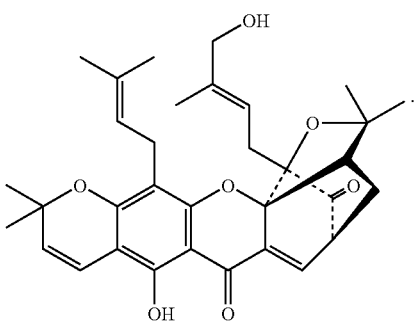

7. Product TSB-7:

Product TSB-7 was determined to have the following properties:

Orange powder; mp 106~109° C. IR$v_{max}$ cm$^{-1}$ (KBr): 3500–2400, 2960, 2920, 1735, 1680, 1650, 1625, 1590, 1430, 1325, 1120, 1040, 870, 735. $^1$H NMR (CDCl$_3$, 400 MHz): δ12.71 (1H, s), 7.51 (1H, d, J=6.8 Hz), 6.49 (1H, d, J=10.0 Hz), 6.05 (1H, t, J=7.0 Hz), 5.39 (1H, d, J=10.0 Hz), 4.99 (1H, d, J=6.0 Hz), 3.45 (1H, dd, J=6.4, 4.7 Hz), 3.27 (1H, m), 3.08 (1H, m), 2.97 (2H, sept, J=8.0 Hz), 2.49 (1H, d, J=9.3 Hz), 2.28 (1H, dd, J=13.4, 4.5 Hz), 1.70, 1.69, 1.67, 1.60, 1.36, 1.34, 1.26 (each 3H, s) $^{13}$C NMR (CDCl$_3$, 100 MHz): δ203.47, 179.07, 171.74, 161.22, 157.65, 157.34, 138.46, 135.39, 133.42, 131.46, 127.64, 126.00, 122.22, 115.44, 108.04, 103.16, 100.55, 90.93, 83.82, 78.55, 49.01, 46.80, 29.87, 29.26, 28.82, 28.40, 28.20, 25.68, 25.14, 21.57, 20.63, 18.06.

EIMSm/z (relative intensity): 560[M]$^+$(100), 545(56), 532(63), 517(48), 487(12), 433(9), 405(81), 391(22), 363(38), 349(24), 307(18), 287(64), 245(40), 231(21), 215(20), 189(10).

According to the analyzed spectroscopic data, product TSB-7 was identified to be a known compound having the following chemical structure, i.e., morellic acid:

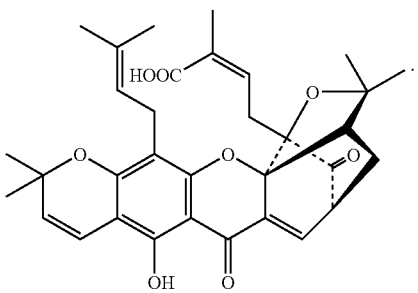

8. Product TSB-8:

Product TSB-8 was determined to have the following properties:

Orange needles; mp 109~110° C. $^1$H NMR (CDCl$_3$, 400 MHz): δ12.89 (1H, s), 7.45 (1H, d, J=7.2 Hz), 7.27 (1H, 3), 6.65 (1H, d, J=10.4 Hz), 5.53 (1H, d, J=9.6 Hz), 5.30 (1H, br d, J=6.0 Hz), 4.43 (1H, br s), 3.49 (1H, m), 3.32 (2H, m), 2.50 (2H, m), 2.34 (1H, m), 1.78, 1.71, 1.68, 1.59, 1.33, 1.03 (each 3H, s), 1.45 (6H, s).

EIMSm/z (relative intensity): 530[M]$^+$(100), 515(22), 502(92), 488(30), 487(83), 459(11), 433(20), 405(49), 391(15), 363(24), 349(16), 307(13), 287(27), 231(13), 215(37), 189(6).

According to the analyzed spectroscopic data, product TSB-8 was identified to be a known compound having the following chemical structure, i.e., desoxymorellin:

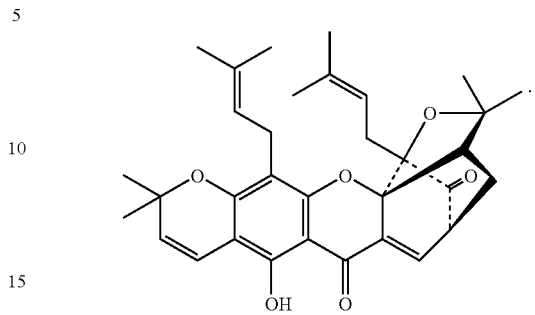

9. Product TSB-4:

Product TSB-4 was determined to have the following properties:

Yellow needles; mp 115~118° C. The result was positive when subjected to FeCl$_3$ test, which indicates that it is a phenolic compound. IR$v_{max}$ cm$^{-1}$ (KBr): 3640, 3450, 3150, 2960, 2900, 1632, 1602, 1570, 1500, 1460, 1420, 1395, 1340, 1295, 1230, 1130, 1055, 870, 825, 790. $^1$H NMR (acetone-d$_6$, 600 MHz): δ13.09 (1H, s, OH-1), 7.40 (1H, s, H-8), 6.55 (1H, d, J=10.0 Hz, H-11), 6.32 (1H, s, H-2), 5.87 (1H, d, J=10.0 Hz, H-12), 5.36 (H, m, H-17), 3.55 (2H, d, J=7.3 Hz, H$_2$-16), 1.84 (3H, s, H-20), 1.63 (3H, s, H-19), 1.48 (6H, s, H$_3$-14, H$_3$-15). $^{13}$C NMR (acetone-d$_6$, 125 MHz): δ181.24 (C=O), 163.41 (C-3), 162.26 (C-1), 155.56 (C-4a), 146.94 (C-6), 146.43 (C-10a), 134.42 (C-18), 132.30 (C-12), 131.77 (C-5), 123.33 (C-17), 122.08 (C-11), 119.03 (C-7), 115.20 (C-8a), 113.15 (C-8), 107.54 (C-4), 103.26 (C-9a), 98.40 (C-2), 78.84 (C-13), 28.26 (C-14,15), 25.93 (C-19), 22.16 (C-16), 18.00 (C-20).

EIMSm/z (relative intensity): 394[M]$^+$(66), 393(23), 379 (100), 339(30), 323(16), 311(13), 295(5), 278(10), 203(4), 162 (7).

The EIMS data of product TSB-4 show a molecular peak [M]$^+$ at m/z 394, which corresponds to xanthone represented by the molecular formula C$_{23}$H$_{22}$O$_6$.

The $^1$H NMR spectrum of product TSB-4 shows that it has a chelated hydroxy group) (δ13.09), two singlets of aromatic protons [δ6.32 (1H, s) and δ7.40 (1H, s)], a singlet of two methyl protons [δ1.48 (6H, s)], and two cis-olefinic protons coupled to each other [δ5.87 (1H, d, J=10 Hz) and δ6.55 (1H, d, J=10 Hz)]. These signals indicate that a dimethyl chromene ring is present in the molecular structure of product TSB-4.

In addition, it is known from the $^1$H NMR spectrum data of product TSB-4 that there are two vinyl methyl protons [δ 1.63 (3H, s) and δ1.84 (3H, s)], methylene protons [δ3.55 (2H, d, J=7.3 Hz)], and olefinic proton [δ5.36 (1H, m)]. This indicates that the molecular structure of product TSB-4 includes a γ,γ-dimethylallyl chain.

From the above data, it is known that substitutes of a 2,2-dimethylpyran ring and a γ,γ-dimethylallyl chain are present in the structure of xanthone of product TSB-4.

Apart from using 2D-NMR, Homonuclear Correlation Spectroscopy, $^1$H-$^1$H COSY, to verify the coupling in the aforesaid $^1$H NMR spectrum, it is found from $^1$H-Detected heteronuclear multiple-quantum coherence (HMQC) (J=150 Hz) that: δ7.40 and δ113.15 are correlated; δ6.32 and δ98.40 are correlated; δ56.55 and δ122.08 are correlated; and δ5.87 and δ132.30 are correlated. This shows that the chemical shifts of the two disubstituted olefinic carbons in the pyran ring are δ122.08 and δ132.30. In addition, δ5.36 of trisubstituted olefinic proton and δ123.33 are correlated, and the methylene protons (δ3.55) coupled therewith are correlated with δ22.16.

In addition, it is also found from $^1$H-Detected multiple-bond heteronuclear multiple-quantum coherence (HMBC) (J=8 Hz) spectral data of product TSB-4 that chelated hydroxy group (δ13.09) and two quaternary carbons (δ103.26 and δ162.26) are correlated, and are additionally correlated with an unsubstituted aromatic ring carbon (δ98.40). This proves that the C-2 position of the xanthone skeleton is not substituted by hydroxy. C-2 proton signal δ6.32 and two quaternary carbons (δ103.26, 107.54) are correlated, and are additionally correlated with two hydroxy-bonded quaternary carbons (δ163.41, 162.26). Methylene proton (δ3.55) and quaternary carbons (δ163.41, 155.56, 134.42, and δ107.54) are correlated, and are correlated with a tertiary carbon (δ123.33). This proves that γ,γ-dimethylallyl chain is connected to the C-4 position. Therefore, the A ring in the xanthone skeleton is substituted by [1,3-dihydroxy-4-(γ,γ-dimethylallyl)].

It is found from HMBC spectrum that another aromatic proton (δ7.40) is correlated to carbonyl carbon (δ181.24) and two oxygen-bonded carbons (δ146.43, δ146.94), and is correlated to one (δ122.08) of the olefinic carbons in the pyran ring. It can thus be seen that the proton (δ7.40) is located at C-8, i.e., the peri-position of the carbonyl group, and that the pyran ring to which is bonded and the xanthone skeleton must be coupled in a linear form. It is only possible for the last remaining hydroxy to be bonded to the C-5 position, and the chemical shift of the $^{13}$C NMR spectrum thereof is δ131.77.

In view of the foregoing data, product TSB-4 is identified to be a new compound having the following chemical structure:

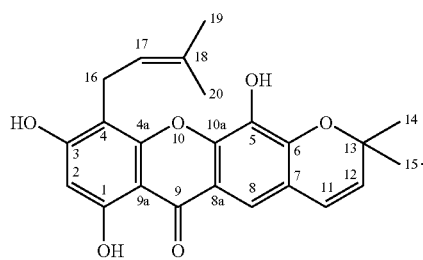

Product TSB-4 is identified by the name formoxanthone A {IUPAC nomenclature: [1,3,5-trihydroxy-6',6'-dimethyl-2H-pyrano(2',3':6,7)-4-(3-methylbut-2-enyl)xanthone]or [7,9,12-trihydroxy-2,2-dimethyl-10-(3-methyl-but-2-enyl)-2H-pyrano[3,2-b]xanthen-6-one]}.

Identification of Constituents of Acetone-Extracted Product TSB-14 from Gamboge Resin To further understand the distribution of the constituents of acetone-extracted product TSB-14 from gamboge resin, an HPLC analysis was conducted by referring to the general procedures described herein above. The results thus obtained are shown in FIG. 1.

Figure 2:
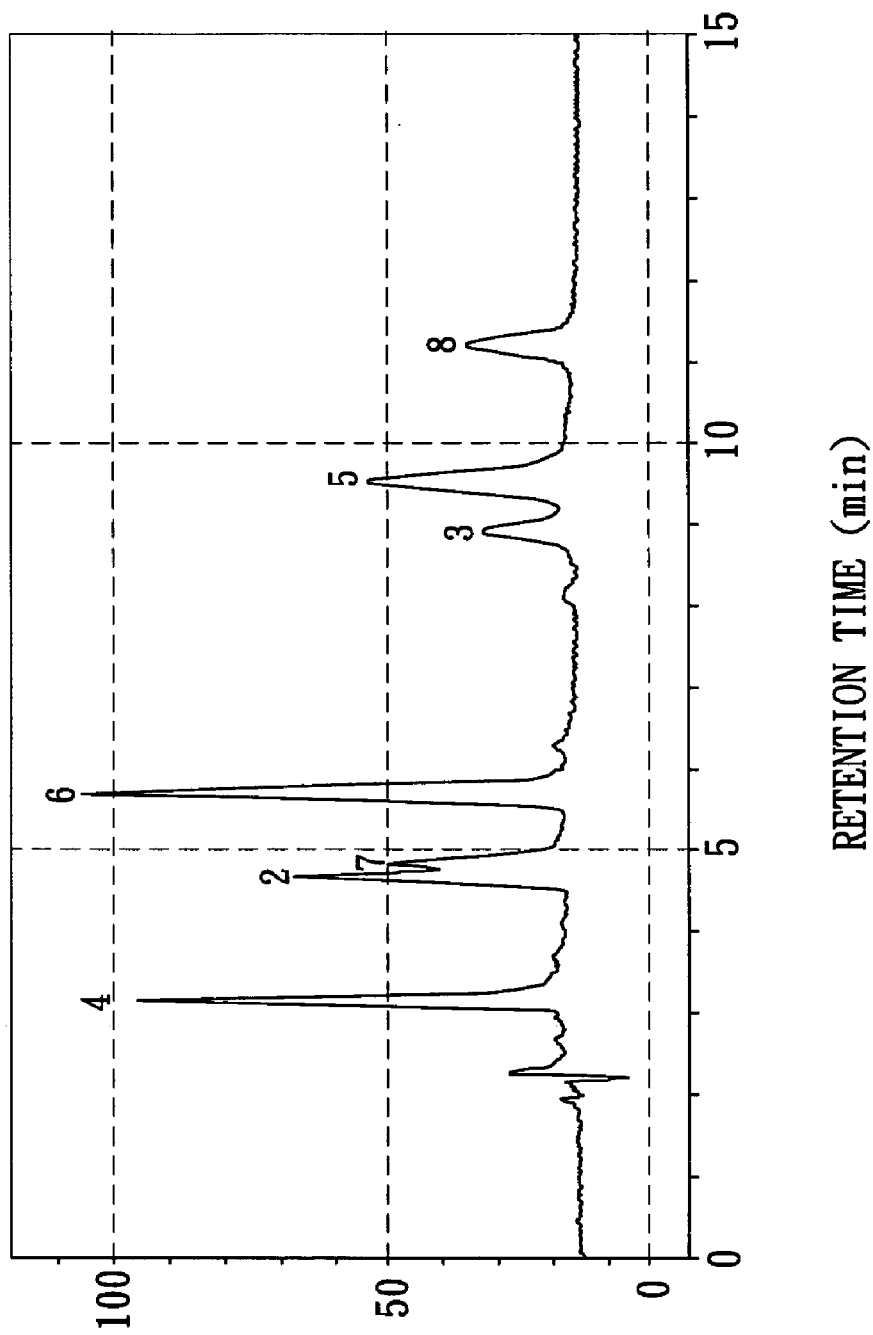
FIG. 2 is an HPLC elution profile, in which 7 products (respectively identified as TSB-2 to TSB-8 in the following description) purified from gamboge resin according to this invention are utilized as standard products for conducting HPLC analyses, and the numbers at the peaks correspond to the numbers of the respective products TSB2 to TSB-8.

Since TSB-0 and TSB-1 do not have the characteristic of UV light absorption, the seven purified compounds TSB-2 to TSB-8 were used as standard compounds for the HPLC analysis, thereby resulting in an HPLC elution profile as shown in FIG. 2, in which the numbers for peaks correspond respectively to the numbers of the products, TSB-2 to TSB-8.

Figure 3:
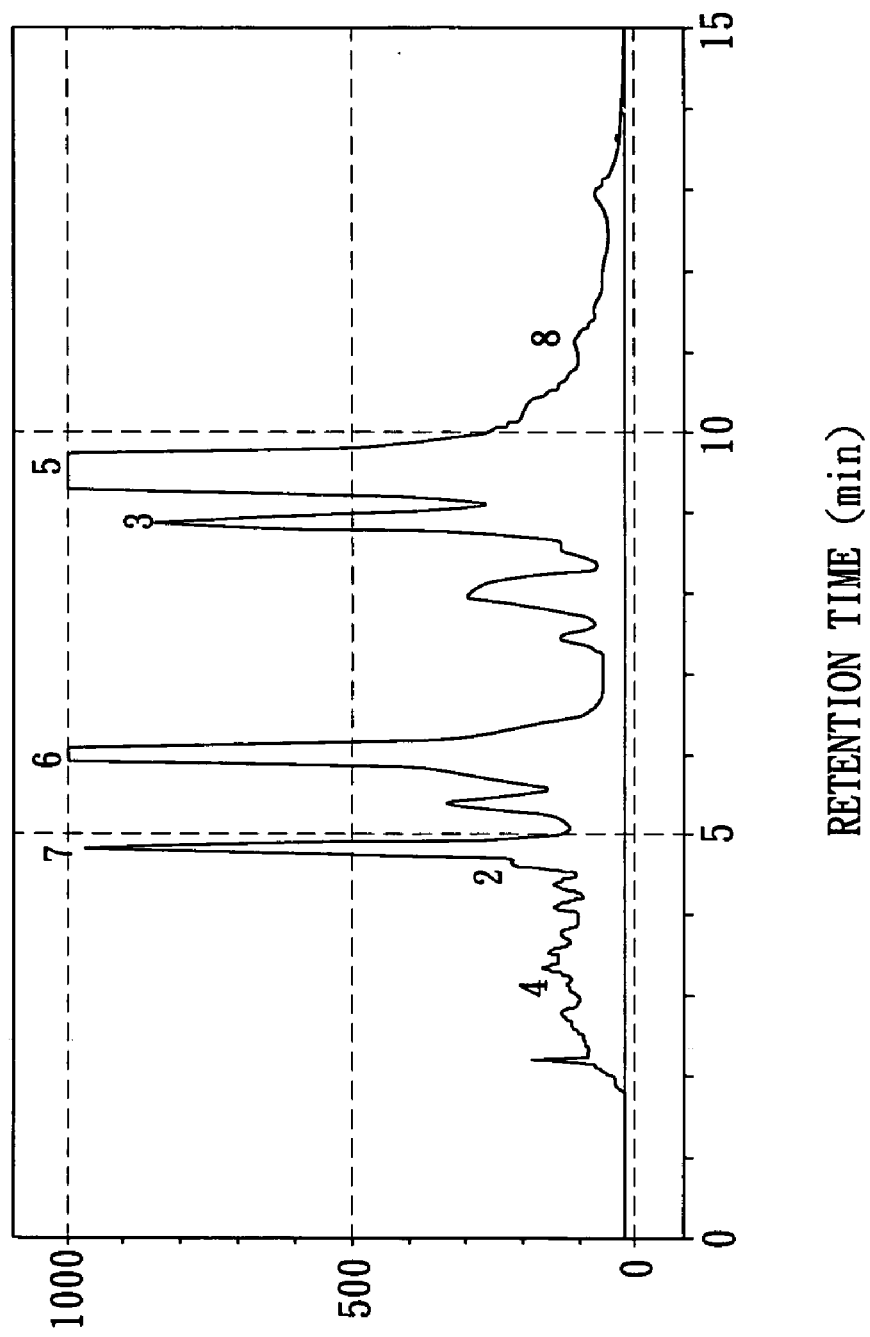
FIG. 3 is an HPLC elution profile, which shows results of comparison of FIGS. 1 and 2 for illustrating to which of the peaks in the elution profile of TSB-14 the seven products TSB-2 to TSB-8 correspond, in which the sample concentration of product TSB-14 was up-adjusted to facilitate comparison.

To find out the peaks in the elution profile of the acetone-extracted product TSB-14 to which products TSB-2 to TSB-8 respectively correspond, the concentration of the sample of the acetone-extracted product TSB-14 was increased to obtain an HPLC elution profile as shown in FIG. 3.

Figure 4:
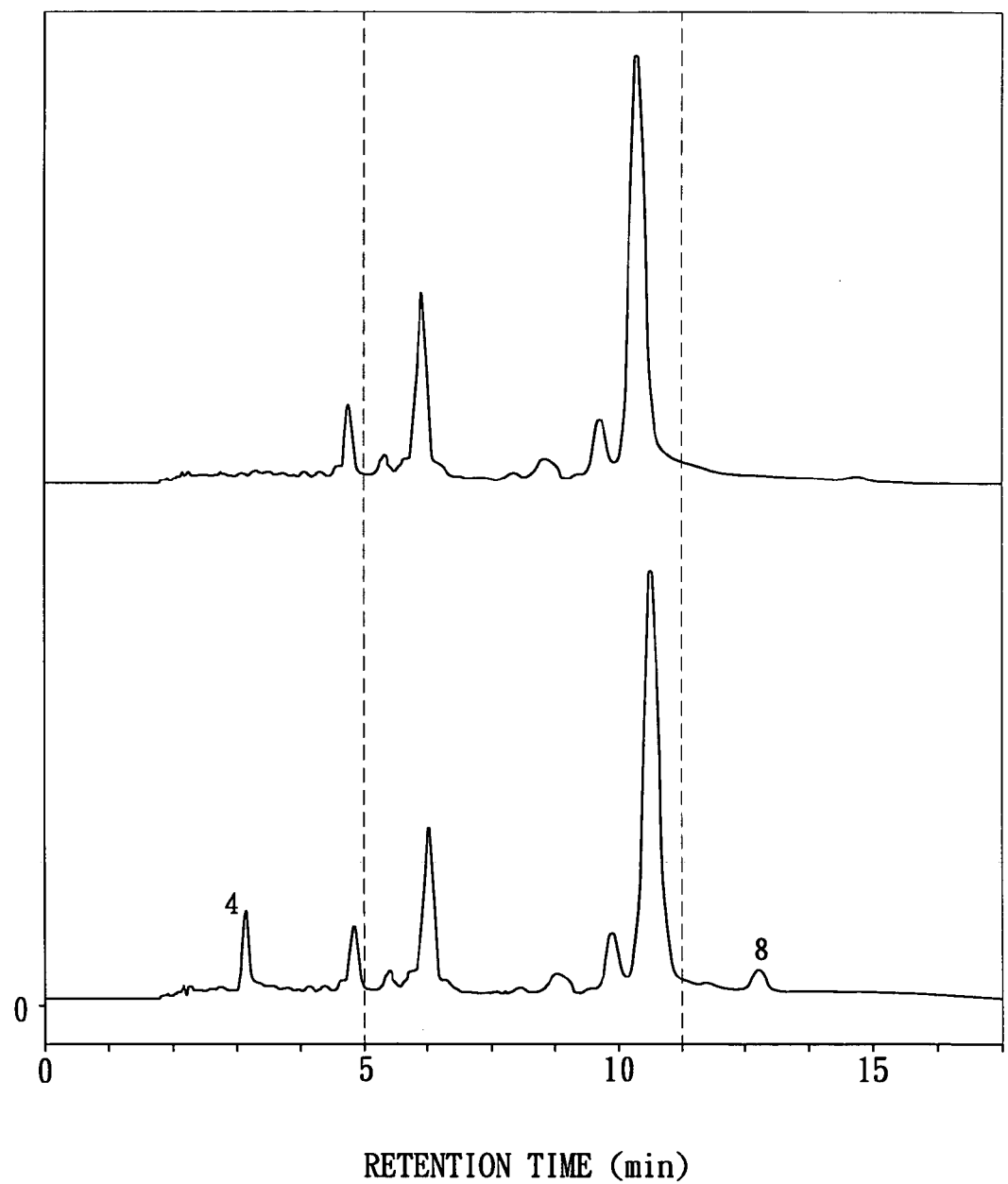
FIG. 4 is an HPLC elution profile showing the HPLC result (upper side) of product TSB-14 according to this invention, and the HPLC results (lower side) of product TSB-14 supplemented with 500 µl each of product TSB-4 acetone solution and product TSB-8 acetone solution, for identifying the elution peaks corresponding to products TSB-4 and TSB-8.

By comparing the results in FIGS. 1 to 3, it is found that the contents of TSB-4 and TSB-8 in TSB-14 apparently are not high, so that the corresponding peaks as shown in HPLC elution profile are quite low. In order to confirm the positions of the peaks of TSB-4 and TSB-8, acetone-extracted product TSB-14 (above) and acetone-extracted product TSB-14 added with TSB-4 (500 μl) and TSB-8 (500 μl) (below) were used to conduct HPLC, thereby obtaining an HPLC elution profile as shown in FIG. 4.

Figure 5:
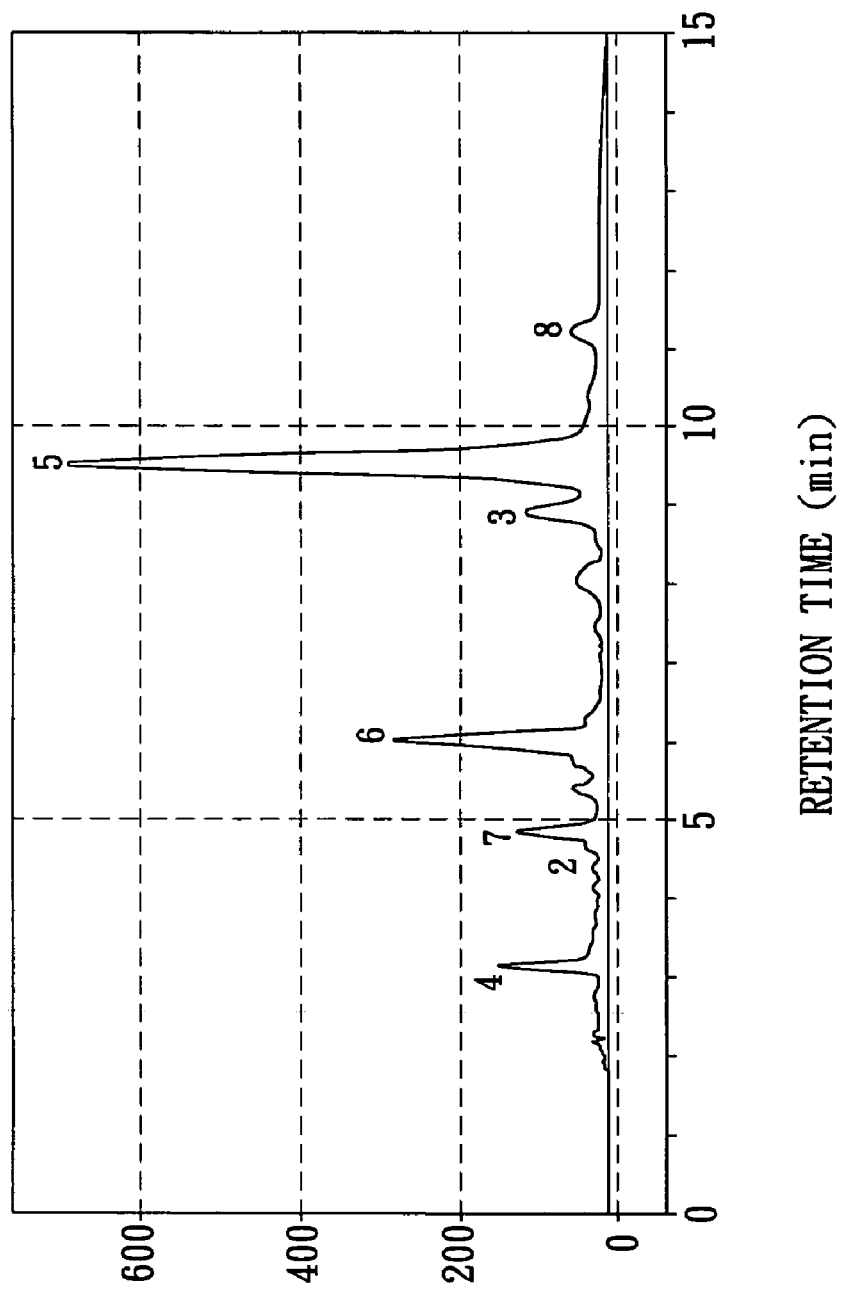
FIG. 5 is an HPLC elution profile showing the corresponding positions of the seven products TSB-2 to TSB-8 purified from gamboge resin according to this invention in the elution profile of product TSB-14 according to this invention.

To display the corresponding positions of the seven products TSB-2 to TSB-8 that were purified from gamboge resin according to this invention in the elution profile of product TSB-14 according to this invention, an HPLC elution profile as shown in FIG. 5 was obtained.

Therefore, it can be confirmed from the HPLC results that the acetone-extracted product TSB-14 obtained from gamboge resin according to this invention includes the following nine compounds: betulin (TSB-0), betulinic acid (TSB-1), isomorellic acid (TSB-2), isogambogic acid (TSB-3), formoxanthone A (TSB-4), gambogic acid (TSB-5), isomorellinol (TSB-6), morellic acid (TSB-7), and desoxymorellin (TSB-8). In addition to the aforesaid nine purified compounds, the acetone-extracted product TSB-14 further includes approximately 25% minor constituents, including triterpenes and xanthones, as well as other unidentified compounds.

Example 4

Pharmacological Experiments of Acetone-Extracted Product and Purified Compounds from Gamboge Resin In order to determine the biological activity of the acetone-extracted product TSB-14 of this invention and products TSB-1 to TSB-8 purified from said extract, the following pharmacological activity analyses were conducted.

Pharmacological Exp. 1 in Vitro Anti-Cancer Test

The cancer cell growth inhibition test was primarily used to detect the effect of a candidate drug on cancer cell proliferation. The working principle involved therein is the ability of viable cells to shift alamarBlue (Biosource, USA) from its originally non-fluorescent oxidized state to a reduced form (fluorescent, red) having fluorescence via metabolic reaction. According to the fluorescent data result generated by the alamarBlue reagent thus obtained, the proliferation of the viable cells and cell activity can be quantified for detection.

In this experiment, the assay concentrations of the candidate drug were set to be 0.01, 0.1, 1, 10, and 100 μg/ml, and the following cell lines were used: 6 human cancer cells MCF-7 (breast cancer), HT-29 (colon cancer), HL-60 (leukemia), HepG2 (liver cancer), A549 (lung cancer), and U937 (lymphoma cancer), and a normal human umbilical venal epithelial cell (HUVEC). In addition, DMSO (40%) was used as a negative control, and mitomycin was used as a positive control.

The $IC_{50}$ value (50% cell growth inhibition concentration) and the $LC_{50}$ value (50% cell destroying lethal concentration) of the acetone-extracted product TSB-14 according to this invention and products TSB-1 to TSB-8 purified from said extract in respect of the six human cancer cell lines mentioned above and one normal human cell are respectively shown in the following table 1.

TABLE 1

$IC_{50}$ (μg/ml) and $LC_{50}$ (μg/ml) of acetone-extracted product TSB-14 from gamboge resin with respect to cancer cells

| | $IC_{50}$ [μg/ml] | | $LC_{50}$ [μg/ml] | |
|---|---|---|---|---|
| Cell lines | TSB-14 | mitomycin (μM) | TSB-14 | mitomycin (μM) |
| MCF-7 | 1.6 | 0.069 | 3.8 | 3.9 |
| HL-60 | 0.93 | 0.039 | 3.1 | 1.8 |
| HepG2 | 1.5 | 0.026 | 3.8 | 2.1 |
| U937 | 0.30 | 0.069 | 4.6 | 2.5 |
| A549 | 0.78 | 0.068 | 6.2 | 1.6 |
| HT-29 | 0.19 | 0.090 | 1.2 | 4.5 |
| HUVEC | 0.72 | 0.24 | 2.8 | 4.3 |

TABLE 2

$IC_{50}$ (μg/ml) of products TSB-1 to TSB-8 purified from gamboge resin with respect to cancer cells

| | Tested products | | | | | | | | |
|---|---|---|---|---|---|---|---|---|---|
| Cell lines | TSB-1 | TSB-2 | TSB-3 | TSB-4 | TSB-5 | TSB-6 | TSB-7 | TSB-8 | Mitomycin(μM) |
| MCF-7 | — | 9.0 | 1.6 | 10 | 0.83 | 0.90 | 0.98 | 5.3 | 0.090 |
| HL-60 | — | 2.3 | 0.97 | 7.7 | 0.50 | 1.4 | 1.2 | 6.5 | 0.047 |
| HepG2 | — | 6.4 | 1.2 | 8.9 | 0.83 | 1.2 | 1.7 | 3.9 | 0.062 |
| U937 | — | 1.6 | 0.82 | 6.9 | 0.65 | 1.3 | 1.6 | 6.2 | 0.035 |
| A549 | >100 | 1.3 | 0.88 | 1.8 | 0.8 | 2.0 | 0.76 | 4.8 | 0.062 |
| HT-29 | >100 | 6.9 | 6.4 | 8.4 | 4.5 | 5.2 | 2.8 | 6.7 | 0.120 |
| HUVEC | — | 1.7 | 1.1 | 11 | 0.87 | 1.5 | 0.88 | 2.8 | 0.055 |

"—" indicates "not determined".

TABLE 3

$LC_{50}$ (μg/ml) of products TSB-1 to TSB-8 further purified from gamboge resin with respect to cancer cells

| | Tested products | | | | | | | | |
|---|---|---|---|---|---|---|---|---|---|
| Cell lines | TSB-1 | TSB-2 | TSB-3 | TSB-4 | TSB-5 | TSB-6 | TSB-7 | TSB-8 | Mitomycin(μM) |
| MCF-7 | — | 24 | 4.3 | 40 | 2.7 | 5.8 | 6.2 | 83 | 2.1 |
| HL-60 | — | 43 | 4.6 | 42 | 5.2 | 6.2 | 5.6 | >100 | 1.4 |
| HepG2 | — | 33 | 1.9 | 24 | 2.7 | 3.0 | 3.9 | 31 | 0.72 |
| U937 | — | 6.1 | 3.1 | 28 | 3.1 | 3.8 | 4.8 | >100 | 1.1 |
| A549 | >100 | 4.6 | 4.8 | 21 | 2.9 | 9.6 | 3.4 | 56 | 1.4 |
| HT-29 | >100 | 12 | 8.8 | 59 | 7.1 | 8.5 | 7.2 | 69 | 4.2 |
| HUVEC | — | 22 | 5.2 | 21 | 3.6 | 9.3 | 4.8 | 40 | 1.6 |

"—" indicates "not tested".

It is known from the results shown in Tables 1 to 3 that the acetone-extracted product TSB-14 according to this invention and the products TSB-2 to TSB-8 purified from said extract evidently have the effects of inhibiting tumor cell growth and thus are highly promising anti-cancer drugs.

Pharmacological Exp. 2 in Vitro Anti-Cancer Effect of Mixture Formulations Containing Products TSB-0 to TSB-8

In order to further understand the bioactivity of the products TSB-0 to TSB-8 of this invention when they are used in combination, mixture formulations TSB-9, TSB-10, TSB-11, TSB-12 and TSB-13 were prepared according to Table 4 below. The results obtained are shown in Tables 5 to 9, respectively.

TABLE 4

| Constituents (%) | Mixture formulations | | | | |
|---|---|---|---|---|---|
| | TSB-9 | TSB-10 | TSB-11 | TSB-12 | TSB-13 |
| TSB-14 | 90 | 0 | 0 | 0 | 0 |
| TSB-1 | 0 | 10 | 10 | 10 | 10 |
| TSB-2 | 0 | 0 | 20 | 0 | 30 |
| TSB-3 | 0 | 20 | 0 | 0 | 40 |
| TSB-4 | 0 | 5 | 5 | 5 | 5 |
| TSB-5 | 0 | 50 | 0 | 40 | 0 |
| TSB-6 | 0 | 0 | 5 | 0 | 5 |
| TSB-7 | 0 | 0 | 50 | 30 | 0 |
| TSB-8 | 0 | 5 | 0 | 5 | 0 |
| Sorbitol | 0 | 2.5 | 2.5 | 2.5 | 2.5 |
| Mannitol | 0 | 2.5 | 2.5 | 2.5 | 2.5 |
| Lactose | 0 | 2.5 | 2.5 | 2.5 | 2.5 |
| Sucrose | 0 | 2.5 | 2.5 | 2.5 | 2.5 |
| Corn starch | 0 | 0 | 0 | 0 | 0 |

TABLE 4-continued

| Constituents (%) | Mixture formulations | | | | |
|---|---|---|---|---|---|
| | TSB-9 | TSB-10 | TSB-11 | TSB-12 | TSB-13 |
| Crystalline cellulose | 0 | 0 | 0 | 0 | 0 |
| Brown sugar | 10 | 0 | 0 | 0 | 0 |

TABLE 5

Effect of formulation TSB-9 on inhibiting cancer cell growth

| Cell lines | TSB-9 (μg/ml) | | Mitomycin (μM) | |
|---|---|---|---|---|
| | $IC_{50}$ | $LC_{50}$ | $IC_{50}$ | $LC_{50}$ |
| MCF-7 | 2.7 | 5.7 | 0.034 | 2.30 |
| HL-60 | 0.57 | 8.8 | 0.027 | 0.70 |
| HepG2 | 1.7 | 5.8 | 0.036 | 1.30 |
| U937 | 0.29 | 2.0 | 0.056 | 0.59 |
| A549 | 0.72 | 3.7 | 0.061 | 1.20 |
| HT-29 | 0.76 | 5.5 | 0.089 | 4.70 |
| HUVEC | 0.14 | 0.24 | 0.17 | 8.80 |

TABLE 6

Effect of formulation TSB-10 on inhibiting cancer cell growth

| Cell line | TSB-10 (μg/ml) | | Mitomycin (μM) | |
|---|---|---|---|---|
| | $IC_{50}$ | $LC_{50}$ | $IC_{50}$ | $LC_{50}$ |
| MCF-7 | 0.68 | 5.7 | 0.034 | 2.30 |
| HL-60 | 0.78 | 8.8 | 0.027 | 0.70 |
| HepG2 | 1.10 | 5.8 | 0.036 | 1.30 |
| U937 | 0.38 | 2.0 | 0.056 | 0.59 |
| A549 | 0.96 | 3.7 | 0.061 | 1.20 |
| HT-29 | 0.13 | 5.5 | 0.089 | 4.70 |
| HUVEC | 0.71 | 0.24 | 0.170 | 8.80 |

TABLE 7

Effect of formulation TSB-11 on inhibiting cancer cell growth

| Cell line | TSB-11 (μg/ml) | | Mitomycin (μM) | |
|---|---|---|---|---|
| | $IC_{50}$ | $LC_{50}$ | $IC_{50}$ | $LC_{50}$ |
| MCF-7 | 0.72 | 3.7 | 0.069 | 3.9 |
| HL-60 | 0.57 | 6.8 | 0.039 | 1.8 |
| HepG2 | 1.20 | 2.5 | 0.026 | 2.1 |
| U937 | 0.71 | 3.8 | 0.069 | 2.5 |
| A549 | 0.47 | 4.7 | 0.068 | 1.6 |
| HT-29 | 0.47 | 1.8 | 0.090 | 4.5 |
| HUVEC | 0.98 | 6.2 | 0.240 | 4.3 |

TABLE 8

Effect of formulation TSB-12 on inhibiting cancer cell growth

| Cell line | TSB-12 (μg/ml) | | Mitomycin (μM) | |
|---|---|---|---|---|
| | $IC_{50}$ | $LC_{50}$ | $IC_{50}$ | $LC_{50}$ |
| MCF-7 | 0.76 | 3.1 | 0.069 | 3.9 |
| HL-60 | 0.61 | 7.0 | 0.039 | 1.8 |
| HepG2 | 1.10 | 3.0 | 0.026 | 2.1 |
| U937 | 0.80 | 3.5 | 0.069 | 2.5 |
| A549 | 0.24 | 4.8 | 0.068 | 1.6 |
| HT-29 | 0.35 | 1.6 | 0.090 | 4.5 |
| HUVEC | 0.71 | 2.2 | 0.240 | 4.3 |

TABLE 9

Effect of formulation TSB-13 on inhibiting cancer cell growth

| Cell line | TSB-13 (μg/ml) | | Mitomycin (μM) | |
|---|---|---|---|---|
| | $IC_{50}$ | $LC_{50}$ | $IC_{50}$ | $LC_{50}$ |
| MCF-7 | 1.60 | 3.8 | 0.069 | 3.9 |
| HL-60 | 0.93 | 3.1 | 0.039 | 1.8 |
| HepG2 | 1.50 | 3.8 | 0.026 | 2.1 |
| U937 | 0.30 | 4.6 | 0.069 | 2.5 |
| A549 | 0.78 | 6.2 | 0.068 | 1.6 |
| HT-29 | 0.19 | 1.2 | 0.090 | 4.5 |
| HUVEC | 0.72 | 2.8 | 0.240 | 4.3 |

It can be known from the results shown in Tables 5–9 that products TSB-1 to TSB-8 purified from gamboge resin according to this invention clearly exhibited the effect of inhibiting tumor cell growth under different combinations and thus have high potentials of being developed into anti-cancer drugs.

Pharmacological Exp. 3 in Vivo Bioactivity of Mixture Formulation TSB-9

Mixture formulation TSB-9 was further subjected to an animal test, in which female mice (6–8 weeks old, weighing 20–22 grams) originally from C.B-17/Icr background and having Severe Combined Immune Deficiency (SCID) were used.

Human breast cancer cells MCF-7 (ATCC HTB-22) ($1\times10^7$ cells/0.2 ml) were implanted subcutaneously into the dorsal side of the mice, and 50 μg/mouse of estradiol benzoate (Sigma, USA) was injected subcutaneously into the mice weekly as supplement for a total of 4 weeks. When the tumor growth reached ≧5 mm in diameter (that very day was denoted as day 1), tumor-bearing nude mice were randomly divided into 4 groups (6 mice in each group).

Mixture formulation TSB-9 was dissolved in 10% DMSO, and was administered orally to the mice every day at two dosages 40 mg/kg and 80 mg/kg, respectively, for a total of 21 consecutive days. Mitomycin was administered intraperitoneally to the mice at a dose of 2 mg/kg at 4-day interval for a total of 5 doses. This treatment group served as a positive control.

After administration of the test substance, the mice were observed for the following items: signs of overt toxicity, body weight, and tumor size. Measurements were taken once every 4 days during the experiment periods, and were recorded. The experiment results obtained are shown in Table 10 and Table 11.

TABLE 10

In vivo Effect of mixture formulation TSB-9 in inhibiting tumor growth

| Tumor growth | TSB-9 | | mitomycin | Vehicle |
|---|---|---|---|---|
| (% T/C) | 40 mg/kg × 21 | 80 mg/kg × 21 | 2 mg/kg × 5 | (10% DMSO) |
| Day 1 | 102 | 98 | 98 | 100 |
| Day 5 | 81 | 28* | 31* | 100 |
| Day 9 | 62 | 15* | 1* | 100 |
| Day 13 | 69 | 15* | −6* | 100 |
| Day 17 | 74 | −4* | −23* | 100 |
| Day 21 | 66 | −5* | −36* | 100 |

TABLE 10-continued

In vivo Effect of mixture formulation TSB-9 in inhibiting tumor growth

| Tumor growth | TSB-9 | | mitomycin | Vehicle |
|---|---|---|---|---|
| (% T/C) | 40 mg/kg × 21 | 80 mg/kg × 21 | 2 mg/kg × 5 | (10% DMSO) |
| Day 25 | 74 | 9* | −56* | 100 |
| Day 29 | 62 | 9* | −70* | 100 |

*When % T/C ≦ 42%, it indicates significant anti-tumor activity.

TABLE 11

Effect of mixture formulation TSB-9 on body weights of test animals

| Weight (g) (mean ± SEM) | TSB-9 | | mitomycin | Vehicle (10% DMSO) |
|---|---|---|---|---|
| | 40 mg/kg × 21 | 2 mg/kg × 5 | 80 mg/kg × 21 | |
| Day 1 | 22.7 ± 0.7 | 22.5 ± 0.6 | 22.8 ± 0.5 | 22.7 ± 0.5 |
| Day 5 | 21.7 ± 0.7 | 20.8 ± 0.3 | 22.0 ± 0.4 | 22.5 ± 0.4 |
| Day 9 | 21.7 ± 0.819.3 | 19.3 ± 0.4 | 21.7 ± 0.4 | 22.3 ± 0.4 |
| Day 13 | 21.3 ± 0.8 | 19.2 ± 0.3* | 21.0 ± 0.4* | 23/0 ± 0.4 |
| Day 17 | 20.0 ± 0.9 | 18.5 ± 0.2* | 20.2 ± 0.5 | 22.5 ± 0.3 |
| Day 21 | 18.3 ± 0.6 | 17.5 ± 0.2* | 18.2 ± 0.5 | 21.2 ± 0.3 |
| Day 25 | 17.3 ± 0.5 | 16.7 ± 0.2 | 16.8 ± 0.3 | 18.5 ± 0.3 |
| Day 29 | 17.3 ± 0.7 | 16.7 ± 0.4 | 16/3 ± 0.6 | 17.3 ± 0.2 |

*The body weight values of the experimental groups showed significant changes (p < 0.05) relative to the vehicle control group when the unpaired Student test was used for analysis.

During the period of 29 days, the mixture formulation TSB-9 at a dose of 80 mg/kg initiated a significant tumor weight inhibiting effect, whereas the mixture formulation TSB-9 at a dose of 40 mg/kg initiated a medium tumor weight inhibiting effect relative to an excipient control group.

All patents and literature references cited in the present specification are hereby incorporated by reference in their entirety. In case of conflict, the present description, including definitions, will prevail.

While the invention has been described with reference to the above specific embodiments, it is apparent that numerous modifications and variations can be made without departing from the scope and spirit of this invention. It is therefore intended that this invention be limited only as indicated by the appended claims.

We claim:
1. A compound of the formula:

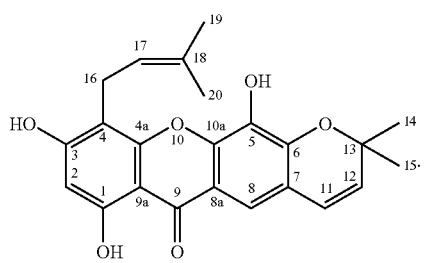

2. A pharmaceutical composition comprising a therapeutically effective amount of a compound according to claim 1.

3. A pharmaceutical composition according to claim 2, further comprising at least a compound selected from the group consisting of betulin, betulinic acid, morellic acid, isomorellic acid, gambogic acid, isogambogic acid, isomorellinol and desoxymorellin.

4. A pharmaceutical composition according to claim 3, which comprises, based on the weight of the composition, 8% of morellic acid, 8% of isomorellic acid, 18% of gambogic acid, 15% of isogambogic acid, 2% of isomorellinol, 4% of desoxymorellin, 8% of betulin, 8% of betulinic acid and 5% of a compound of the formula

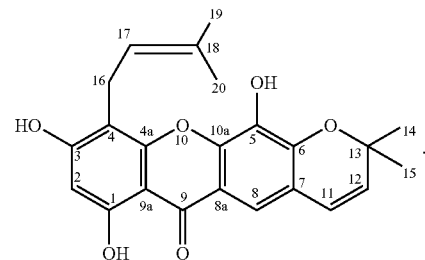

5. A pharmaceutical composition according to claim 3, which comprises, based on the weight of the composition, 10% of betulinic acid, 20% of isogambogic acid, 50% of gambogic acid, 5% of desoxymorellin and 5% of a compound of the formula

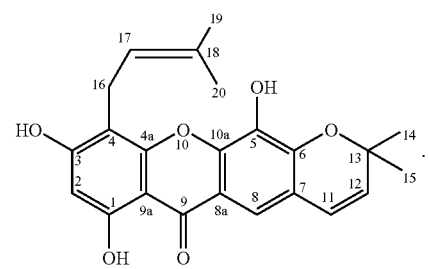

6. A pharmaceutical composition according to claim 3, which comprises, based on the weight of the composition, 10% of betulinic acid, 20% of isomorellic acid, 50% of morellic acid, 5% of isomorellinol and 5% of a compound of the formula

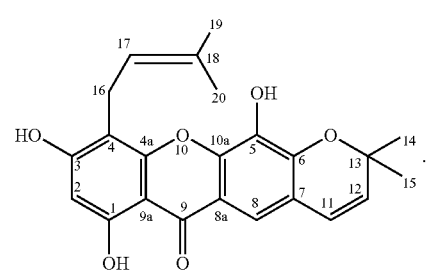

7. A pharmaceutical composition according to claim 3, which comprises, based on the weight of the composition, 10% of betulinic acid, 40% of gambogic acid, 30% of morellic acid, and 5% of desoxymorellin and 5% of a compound of the formula

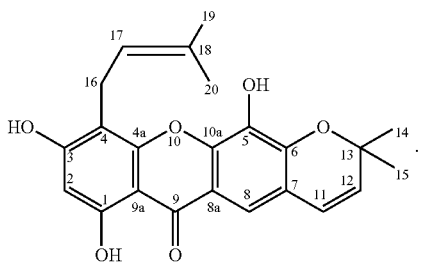

8. A pharmaceutical composition according to claim 3, which comprises, based on the weight of the composition, 10% of betulinic acid, 40% of isogambogic acid, 30% of isomorellic acid, and 5% of isomorellinol and 5% of a compound of the formula

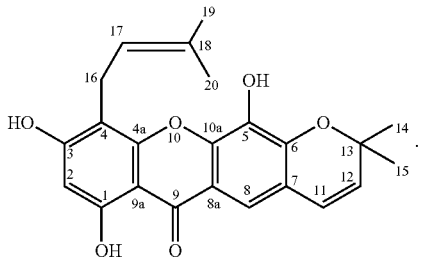

9. A pharmaceutical composition according to claim 2, further comprising a pharmaceutically acceptable carrier.

10. A pharmaceutical composition according to claim 9, wherein the pharmaceutically acceptable carrier includes one or more of the following agents: excipients, solvents, emulsifiers, suspending agents, disintegrating agents, binders, stabilizers, preservatives, lubricants, absorption delaying agents and liposomes.

11. A pharmaceutical composition according to claim 10, wherein the pharmaceutically acceptable carrier is an excipient which includes at least a saccharide compound selected from sucrose, brown sugar, lactose, sorbitol, mannitol, corn starch, and crystalline cellulose.

12. A composition obtained from extraction of gamboge resin with acetone, which comprises a compound according to claim 1, betulin, betulinic acid, morellic acid, isomorellic acid, gambogic acid, isogambogic acid, isomorellinol and desoxymorellin.

13. A pharmaceutical composition comprising a therapeutically effective amount of a product according to claim 12.

14. A pharmaceutical composition according to claim 13, further comprising a pharmaceutically acceptable carrier.

15. A pharmaceutical composition according to claim 14, wherein the pharmaceutically acceptable carrier includes at least one of the following agents: excipients, solvents, emulsifiers, suspending agents, disintegrating agents, binders, stabilizers, preservatives, lubricants, absorption delaying agents and liposomes.

16. A pharmaceutical composition according to claim 15, wherein the pharmaceutically acceptable carrier is an expicient which includes at least a saccharide compound selected from sucrose, brown sugar, lactose, D-sorbitol, D-mannitol, corn starch, and crystalline cellulose.

* * * * *